US009180185B2

(12) United States Patent
Bauss et al.

(10) Patent No.: US 9,180,185 B2
(45) Date of Patent: Nov. 10, 2015

(54) COMBINATION THERAPY OF ANTI-HER3 ANTIBODIES

(71) Applicant: Hoffmann-La Roche Inc., Nutley, NJ (US)

(72) Inventors: Frieder Bauss, Neuhofen (DE); Birgit Bossenmaier, Seefeld (DE); Thomas Friess, Diessen-Dettenhofen (DE); Christian Gerdes, Erlenbach (CH); Max Hasmann, Munich (DE); Marlene Thomas, Penzberg (DE); Martin Weisser, Penzberg (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/151,626

(22) Filed: Jan. 9, 2014

(65) Prior Publication Data
US 2014/0227255 A1   Aug. 14, 2014

(30) Foreign Application Priority Data
Jan. 11, 2013   (EP) ..................................... 13151076

(51) Int. Cl.
A61K 39/395   (2006.01)
C07K 16/28   (2006.01)
C07K 16/32   (2006.01)
A61K 39/00   (2006.01)

(52) U.S. Cl.
CPC ......... A61K 39/3955 (2013.01); C07K 16/2863 (2013.01); C07K 16/32 (2013.01); A61K 2039/505 (2013.01); A61K 2039/507 (2013.01); C07K 2317/41 (2013.01); C07K 2317/565 (2013.01); C07K 2317/73 (2013.01); C07K 2317/732 (2013.01); C07K 2317/92 (2013.01)

(58) Field of Classification Search
None
See application file for complete search history.

(56) References Cited

U.S. PATENT DOCUMENTS

| | | | |
|---|---|---|---|
| 7,744,882 | B2 | 6/2010 | Maihle et al. |
| 8,163,287 | B2 | 4/2012 | Sliwkowski et al. |
| 8,735,551 | B2 | 5/2014 | Garner et al. |
| 8,859,797 | B1 | 10/2014 | Wan et al. |
| 2006/0121044 | A1 | 6/2006 | Amler et al. |
| 2006/0188509 | A1* | 8/2006 | Derynck et al. ............ 424/155.1 |
| 2011/0171222 | A1* | 7/2011 | Bossenmaier et al. ..... 424/138.1 |
| 2012/0107234 | A1 | 5/2012 | Pedersen et al. |
| 2012/0107391 | A1 | 5/2012 | Kelsey et al. |
| 2013/0095172 | A1 | 4/2013 | Alavattam et al. |
| 2013/0195851 | A1 | 8/2013 | Alavattam et al. |
| 2013/0251703 | A1* | 9/2013 | Elis et al. .................. 424/133.1 |
| 2013/0323180 | A1 | 12/2013 | Hasmann et al. |
| 2014/0363429 | A1 | 12/2014 | Chowdhury et al. |
| 2015/0086478 | A1 | 3/2015 | Lantto et al. |

FOREIGN PATENT DOCUMENTS

| | | |
|---|---|---|
| WO | 91/08214 | 6/1991 |
| WO | 97/35885 | 10/1997 |
| WO | 00/78347 | 12/2000 |
| WO | 02/060470 A1 | 8/2002 |
| WO | 03/013602 | 2/2003 |
| WO | 03/080835 | 10/2003 |
| WO | 2006/029275 A2 | 3/2006 |
| WO | 2006/082515 * | 8/2006 |
| WO | 2006/082515 A2 | 8/2006 |
| WO | 2007/077028 | 7/2007 |
| WO | 2008/064884 | 6/2008 |
| WO | 2008/100624 A2 | 8/2008 |
| WO | 2008/150577 A1 | 12/2008 |
| WO | 2009/156179 | 12/2009 |
| WO | 2010/019952 | 2/2010 |
| WO | 2010/052225 A1 | 5/2010 |
| WO | 2010/083470 | 7/2010 |
| WO | 2010/108127 A1 | 9/2010 |
| WO | 2010/115552 | 10/2010 |
| WO | 2010/127181 A1 | 11/2010 |
| WO | 2011/022727 | 2/2011 |
| WO | 2011/044311 | 4/2011 |
| WO | 2011/056124 | 5/2011 |
| WO | 2011/060206 | 5/2011 |
| WO | 2011/076683 | 6/2011 |
| WO | 2011/103242 A1 | 8/2011 |
| WO | 2011/112953 | 9/2011 |
| WO | 2011/136911 | 11/2011 |
| WO | 2012/018404 | 2/2012 |
| WO | 2012/022814 A1 | 2/2012 |
| WO | 2012019024 | 2/2012 |
| WO | 2012/031198 A2 | 3/2012 |
| WO | 2012/044612 | 4/2012 |
| WO | 2012/052230 | 4/2012 |
| WO | 2012/059224 | 5/2012 |
| WO | 2012/059858 | 5/2012 |
| WO | 2012/125864 A2 | 9/2012 |

OTHER PUBLICATIONS

Strome et al., The Oncologist, 2007; 12:1084-95.*
Brand et al., Anticancer Res. 2006; 26:463-70.*
(International Preliminary Examination Report for PCT/EP2010/070062 Jun. 26, 2012).
(International Search Report for PCT/EP2010/070062 Apr. 12, 2011).
(Written Opinion for PCT/EP2010/070062 Jun. 26, 2012).
(Written Opinion for PCT/EP2014/050344) (2014).
Alimandi, M. et al., Oncogene 10:1813-1821 (1995).
Barrett et al., "Amplification of the HER2 gene in breast cancers testing 2+ weak positive by HercepTest immunohistochemistry: . . ." J Clin Pathol 60:690-693 (2007).
Brand, Francois-Xavier et al., "Prospect for Anti-HER2 Receptor Therapy in Breast Cancer" Anticancer Research 26:463-470 (2006).

(Continued)

*Primary Examiner* — Sheela J Huff
(74) *Attorney, Agent, or Firm* — Traci H. Ropp

(57) ABSTRACT

The present invention relates to the combination therapy of anti-HER3 antibodies with certain anti-HER antibodies.

15 Claims, 9 Drawing Sheets

(56) References Cited

OTHER PUBLICATIONS

Garrett et al., "Dual Blockade of HER2 in HER2-0verexpressing Tumor Cells Does Not Completly Eliminate HER3 Function" Clinical Cancer Research 19(3):610-619 (2012).

Hellyer, N.J. et al., "Heregulin-dependent Activation of Phosphoinositide 3-Kinase and Akt via the ErbB2/ErbB3 Co-receptor" J Biol Chem 276:42153-42161 (2001).

Htun van der Horst, E. et al., "Anti-HER-3 MAbs inhibit HER-3-mediated signaling in breast cancer cell lines resistant to anti-HER-2 antibodies" Int J Cancer 115:519-527 (2005).

Kraus et al. et al., "Demonstration of ligand-dependent signaling by the erbB-3 tyrosine kinase and its constitutive activation in human breast tumor cells" P Natl Acad Sci USA 90:2900-2904 (1993).

Kraus et al., "Isolation and characterization of ERBB3, a third member of ERBB/epidermal growth factor receptor family: Evidence for overexpression in a subset of human mammary tumors" P Natl Acad Sci USA 86:9193-9197 (Dec. 1989).

Plowman et al. et al., "Molecular cloning and expression of an additional epidermal growth factor receptor-related gene" P Natl Acad Sci USA 87:4905-4909 (1990).

Robinson et al., "Targeting ErbB2 and ErbB3 with a bispecific single-chain Fv enhances targeting selectivity and induces a therapeutic effect in vitro" Brit J Cancer 99:1415-1425 (2008).

Schaefer, K-L. et al., "Constitutive Activation of Neuregulin/ERBB3 Signaling Pathway in Clear Cell Sarcoma of Soft Tissue" Neoplasia 8:613-622 (2006).

Schoeberl et al., "An ErbB3 antibody, MM-121, is active in cancers with ligand-dependent activation" Cancer Res 70:2485-2494 (Mar. 2010).

Sheng et al., "An activated ErbB3/NRG1 autocrine loop supports in vivo proliferation in ovarian cancer cells" Cancer Cell 17:298-310 (Mar. 2010).

Singer, E. et al., "Identification of a Heregulin Binding Site in HER3 Extracellular Domain" J Biol Chem 276:44266-44274 (2001).

Sliwkowski et al., "Coexpression of erbB2 and erbB3 Proteins Reconstitutes a High Affinity Receptor for Heregulin" J Biol Chem 269(20):14661-14665 (May 20, 1994).

Strome, S.E., et al., "A Mechanistic Perspective of Monoclonal Antibodies in Cancer Therapy Beyond Target-Related Effects" The Oncologist 12:1084-1095 ( 2007).

Treder, M. et al., "Fully human anti-HER3 mAb U3-1287 (AMG 888) demonstrates unique in vitro and in vivo activities versus other HER family inhibitors in NSCLC models" Eur J Cancer Supp. (309 Poster), 6(12) (Oct. 2008).

Tubbs et al., "Discrepancies in Clinical Laboratory Testing of Eligibility for Trastuzumab Therapy: Apparent Immunohistochemical False-Positives Do Not Get the Message" Journal of Clinical Oncology 19(10):2714-2721 ( 2001).

* cited by examiner

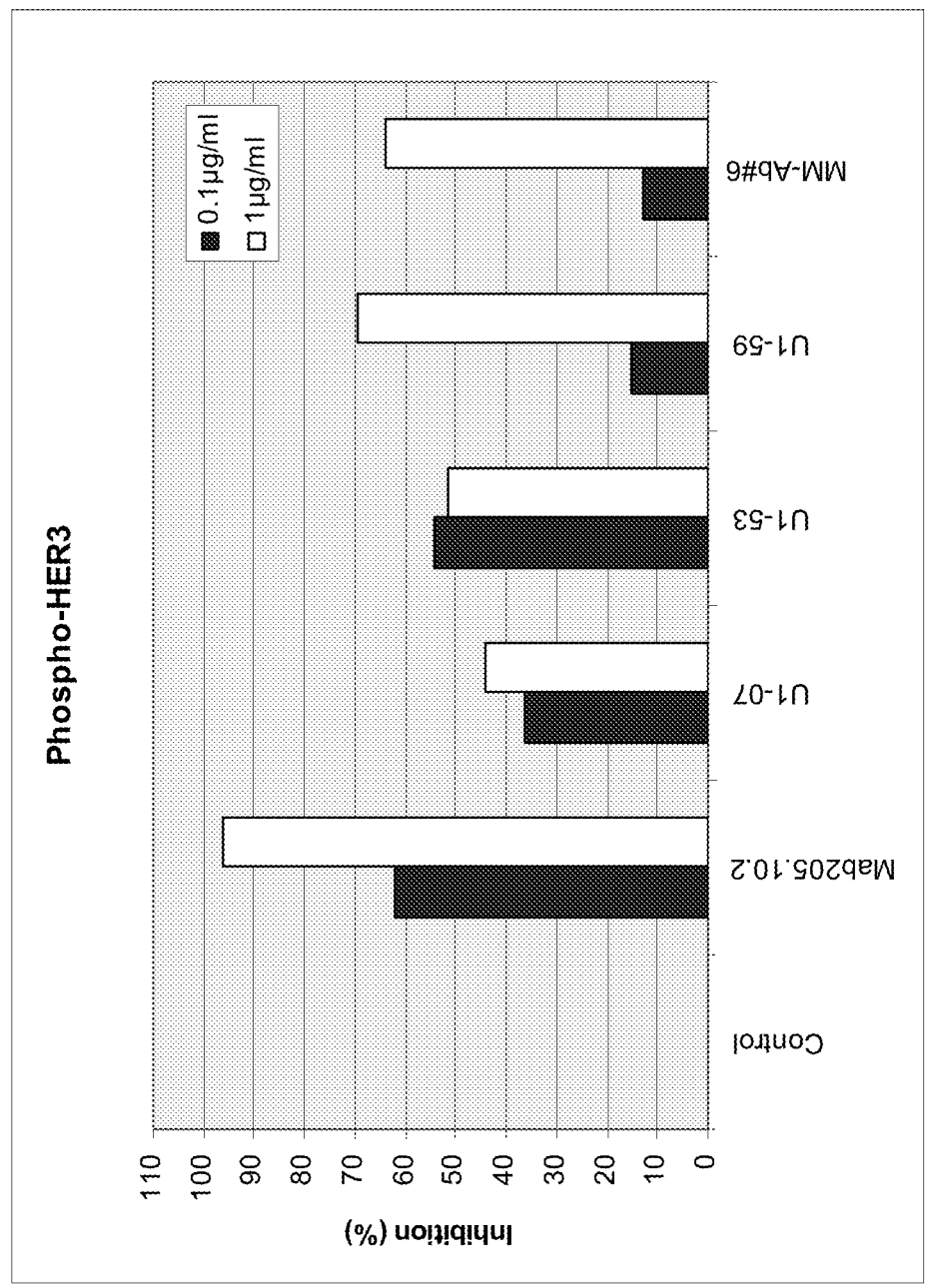

SEQUENCE LISTING

```
<160> NUMBER OF SEQ ID NOS: 21

<210> SEQ ID NO 1
<211> LENGTH: 11
<212> TYPE: PRT
<213> ORGANISM: Artificial
<220> FEATURE:
<223> OTHER INFORMATION: heavy chain CDR3H, Mab 205.10

<400> SEQUENCE: 1

His Arg Asp Tyr Tyr Ser Asn Ser Leu Thr Tyr
1               5                   10

<210> SEQ ID NO 2
<211> LENGTH: 17
<212> TYPE: PRT
<213> ORGANISM: Artificial
<220> FEATURE:
<223> OTHER INFORMATION: heavy chain CDR2H, Mab 205.10

<400> SEQUENCE: 2

Trp Ile Tyr Ala Gly Thr Gly Ser Pro Ser Tyr Asn Gln Lys Leu Gln
1               5                   10                  15

Gly

<210> SEQ ID NO 3
<211> LENGTH: 5
<212> TYPE: PRT
<213> ORGANISM: Artificial
<220> FEATURE:
<223> OTHER INFORMATION: heavy chain CDR1H, Mab 205.10

<400> SEQUENCE: 3

Ser Ser Tyr Ile Ser
1               5
```

```
<210> SEQ ID NO 4
<211> LENGTH: 9
<212> TYPE: PRT
<213> ORGANISM: Artificial
<220> FEATURE:
<223> OTHER INFORMATION: light chain CDR3L, Mab 205.10

<400> SEQUENCE: 4

Gln Ser Asp Tyr Ser Tyr Pro Tyr Thr
1               5

<210> SEQ ID NO 5
<211> LENGTH: 7
<212> TYPE: PRT
<213> ORGANISM: Artificial
<220> FEATURE:
<223> OTHER INFORMATION: light chain CDR2L, Mab 205.10

<400> SEQUENCE: 5

Trp Ala Ser Thr Arg Glu Ser
1               5

<210> SEQ ID NO 6
<211> LENGTH: 17
<212> TYPE: PRT
<213> ORGANISM: Artificial
<220> FEATURE:
<223> OTHER INFORMATION: light chain CDR1L (variant 1), Mab 205.10

<400> SEQUENCE: 6

Lys Ser Ser Gln Ser Leu Leu Asn Ser Gly Asn Gln Lys Asn Tyr Leu
1               5                   10                  15

Thr

<210> SEQ ID NO 7
<211> LENGTH: 17
<212> TYPE: PRT
<213> ORGANISM: Artificial
<220> FEATURE:
<223> OTHER INFORMATION: light chain CDR1L (variant 2), Mab 205.10

<400> SEQUENCE: 7

Lys Ser Ser Gln Ser Val Leu Asn Ser Gly Asn Gln Lys Asn Tyr Leu
1               5                   10                  15

Thr

<210> SEQ ID NO 8
<211> LENGTH: 120
<212> TYPE: PRT
<213> ORGANISM: Artificial
<220> FEATURE:
<223> OTHER INFORMATION: heavy chain variable domain VH, Mab 205.10

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
                20                  25                  30

Tyr Ile Ser Trp Val Arg Gln Ala Pro Gly Gln Gly Leu Glu Trp Met
            35                  40                  45

Gly Trp Ile Tyr Ala Gly Thr Gly Ser Pro Ser Tyr Asn Gln Lys Leu
    50                  55                  60
```

```
Gln Gly Arg Val Thr Met Thr Thr Asp Thr Ser Ser Thr Ala Tyr
 65                  70                  75                  80

Met Glu Leu Arg Ser Leu Arg Ser Asp Thr Ala Val Tyr Tyr Cys
                 85                  90                  95

Ala Arg His Arg Asp Tyr Tyr Ser Asn Ser Leu Thr Tyr Trp Gly Gln
            100                 105                 110

Gly Thr Leu Val Thr Val Ser Ser
            115                 120
```

<210> SEQ ID NO 9
<211> LENGTH: 113
<212> TYPE: PRT
<213> ORGANISM: Artificial
<220> FEATURE:
<223> OTHER INFORMATION: light chain variable domain VL, Mab 205.10.1

<400> SEQUENCE: 9

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Ser
                 85                  90                  95

Asp Tyr Ser Tyr Pro Tyr Thr Phe Gly Gln Gly Thr Lys Leu Glu Ile
             100                 105                 110

Lys
```

<210> SEQ ID NO 10
<211> LENGTH: 113
<212> TYPE: PRT
<213> ORGANISM: Artificial
<220> FEATURE:
<223> OTHER INFORMATION: light chain variable domain VL, Mab 205.10.2

<400> SEQUENCE: 10

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Asn Ser
                 20                  25                  30

Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Ser
                 85                  90                  95

Asp Tyr Ser Tyr Pro Tyr Thr Phe Gly Gln Gly Thr Lys Leu Glu Ile
             100                 105                 110

Lys
```

```
<210> SEQ ID NO 11
<211> LENGTH: 113
<212> TYPE: PRT
<213> ORGANISM: Artificial
<220> FEATURE:
<223> OTHER INFORMATION: light chain variable domain VL, Mab 205.10.3

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ser Ile Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys

<210> SEQ ID NO 12
<211> LENGTH: 107
<212> TYPE: PRT
<213> ORGANISM: Homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 330
<212> TYPE: PRT
<213> ORGANISM: Artificial
<220> FEATURE:
<223> OTHER INFORMATION: human heavy chain constant region derived from
      IgG1 mutated on L234A and L235A

<400> SEQUENCE: 14

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

-continued

```
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325
```

<210> SEQ ID NO 16
<211> LENGTH: 327
<212> TYPE: PRT
<213> ORGANISM: Artificial
<220> FEATURE:
<223> OTHER INFORMATION: human heavy chain constant region derived from IgG4 mutated onS228P

<400> SEQUENCE: 16

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
```

-continued

```
            145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 17
<211> LENGTH: 1342
<212> TYPE: PRT
<213> ORGANISM: homo sapiens

<400> SEQUENCE: 17

Met Arg Ala Asn Asp Ala Leu Gln Val Leu Gly Leu Leu Phe Ser Leu
1               5                   10                  15
Ala Arg Gly Ser Glu Val Gly Asn Ser Gln Ala Val Cys Pro Gly Thr
            20                  25                  30
Leu Asn Gly Leu Ser Val Thr Gly Asp Ala Glu Asn Gln Tyr Gln Thr
        35                  40                  45
Leu Tyr Lys Leu Tyr Glu Arg Cys Glu Val Val Met Gly Asn Leu Glu
    50                  55                  60
Ile Val Leu Thr Gly His Asn Ala Asp Leu Ser Phe Leu Gln Trp Ile
65                  70                  75                  80
Arg Glu Val Thr Gly Tyr Val Leu Val Ala Met Asn Glu Phe Ser Thr
                85                  90                  95
Leu Pro Leu Pro Asn Leu Arg Val Val Arg Gly Thr Gln Val Tyr Asp
            100                 105                 110
Gly Lys Phe Ala Ile Phe Val Met Leu Asn Tyr Asn Thr Asn Ser Ser
        115                 120                 125
His Ala Leu Arg Gln Leu Arg Leu Thr Gln Leu Thr Glu Ile Leu Ser
    130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                165                 170                 175
Lys Asp Asn Gly Arg Ser Cys Pro Pro Cys His Glu Val Cys Lys Gly
            180                 185                 190
```

```
Arg Cys Trp Gly Pro Gly Ser Glu Asp Cys Gln Thr Leu Thr Lys Thr
            195                 200                 205
Ile Cys Ala Pro Gln Cys Asn Gly His Cys Phe Gly Pro Asn Pro Asn
        210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
    370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
            420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
    450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
            500                 505                 510
Gly Pro Gly Gln Cys Leu Ser Cys Arg Asn Tyr Ser Arg Gly Gly Val
        515                 520                 525
Cys Val Thr His Cys Asn Phe Leu Asn Gly Glu Pro Arg Glu Phe Ala
    530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Ser Cys Pro His Gly
            580                 585                 590
Val Leu Gly Ala Lys Gly Pro Ile Tyr Lys Tyr Pro Asp Val Gln Asn
        595                 600                 605
Glu Cys Arg Pro Cys His Glu Asn Cys Thr Gln Gly Cys Lys Gly Pro
```

```
                610                 615                  620
Glu Leu Gln Asp Cys Leu Gly Gln Thr Leu Val Leu Ile Gly Lys Thr
625                 630                 635                  640

His Leu Thr Met Ala Leu Thr Val Ile Ala Gly Leu Val Ile Phe
                645                 650                 655

Met Met Leu Gly Gly Thr Phe Leu Tyr Trp Arg Gly Arg Ile Gln
                660                 665                 670

Asn Lys Arg Ala Met Arg Arg Tyr Leu Glu Arg Gly Glu Ser Ile Glu
                675                 680                 685

Pro Leu Asp Pro Ser Glu Lys Ala Asn Lys Val Leu Ala Arg Ile Phe
                690                 695                 700

Lys Glu Thr Glu Leu Arg Lys Leu Lys Val Leu Gly Ser Gly Val Phe
705                 710                 715                  720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
                740                 745                 750

Phe Gln Ala Val Thr Asp His Met Leu Ala Ile Gly Ser Leu Asp His
                755                 760                 765

Ala His Ile Val Arg Leu Leu Gly Leu Cys Pro Gly Ser Ser Leu Gln
770                 775                 780

Leu Val Thr Gln Tyr Leu Pro Leu Gly Ser Leu Leu Asp His Val Arg
785                 790                 795                  800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
                835                 840                 845

Gln Val Ala Asp Phe Gly Val Ala Asp Leu Leu Pro Pro Asp Asp Lys
850                 855                 860

Gln Leu Leu Tyr Ser Glu Ala Lys Thr Pro Ile Lys Trp Met Ala Leu
865                 870                 875                  880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
                900                 905                 910

Ala Gly Leu Arg Leu Ala Glu Val Pro Asp Leu Leu Glu Lys Gly Glu
                915                 920                 925

Arg Leu Ala Gln Pro Gln Ile Cys Thr Ile Asp Val Tyr Met Val Met
930                 935                 940

Val Lys Cys Trp Met Ile Asp Glu Asn Ile Arg Pro Thr Phe Lys Glu
945                 950                 955                  960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
                980                 985                 990

His Gly Leu Thr Asn Lys Lys Leu  Glu Glu Val Glu Leu  Glu Pro Glu
                995                 1000                1005

Leu Asp Leu Asp Leu Asp Leu  Glu Ala Glu Glu Asp  Asn Leu Ala
    1010                1015                1020

Thr Thr Thr Leu Gly Ser Ala  Leu Ser Leu Pro Val  Gly Thr Leu
    1025                1030                1035
```

```
Asn Arg Pro Arg Gly Ser Gln Ser Leu Leu Ser Pro Ser Ser Gly
    1040                1045                1050

Tyr Met Pro Met Asn Gln Gly Asn Leu Gly Glu Ser Cys Gln Glu
    1055                1060                1065

Ser Ala Val Ser Gly Ser Ser Glu Arg Cys Pro Arg Pro Val Ser
    1070                1075                1080

Leu His Pro Met Pro Arg Gly Cys Leu Ala Ser Glu Ser Ser Glu
    1085                1090                1095

Gly His Val Thr Gly Ser Glu Ala Glu Leu Gln Glu Lys Val Ser
    1100                1105                1110

Met Cys Arg Ser Arg Ser Arg Ser Arg Ser Pro Arg Pro Arg Gly
    1115                1120                1125

Asp Ser Ala Tyr His Ser Gln Arg His Ser Leu Leu Thr Pro Val
    1130                1135                1140

Thr Pro Leu Ser Pro Pro Gly Leu Glu Glu Glu Asp Val Asn Gly
    1145                1150                1155

Tyr Val Met Pro Asp Thr His Leu Lys Gly Thr Pro Ser Ser Arg
    1160                1165                1170

Glu Gly Thr Leu Ser Ser Val Gly Leu Ser Ser Val Leu Gly Thr
    1175                1180                1185

Glu Glu Glu Asp Glu Asp Glu Glu Tyr Glu Tyr Met Asn Arg Arg
    1190                1195                1200

Arg Arg His Ser Pro Pro His Pro Pro Arg Pro Ser Ser Leu Glu
    1205                1210                1215

Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 18
<211> LENGTH: 1255
<212> TYPE: PRT
<213> ORGANISM: homo sapiens

<400> SEQUENCE: 18

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
```

```
            35                  40                  45
Leu Tyr Gln Gly Cys Gln Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                     85                  90                  95

Gln Arg Leu Arg Ile Val Arg Gly Thr Gln Leu Phe Glu Asp Asn Tyr
                    100                 105                 110

Ala Leu Ala Val Leu Asp Asn Gly Asp Pro Leu Asn Asn Thr Thr Pro
                115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460
```

```
Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880
```

```
Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
        900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
        980                 985                 990

Asp Leu Gly Pro Ala Ser Pro Leu Asp Ser Thr Phe Tyr Arg Ser Leu
        995                1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Pro Thr Ala Glu Asn Pro Glu Tyr
    1235                1240                1245

Leu Gly Leu Asp Val Pro Val
    1250                1255

<210> SEQ ID NO 19
<211> LENGTH: 1210
<212> TYPE: PRT
```

```
<213> ORGANISM: homo sapiens

<400> SEQUENCE: 19

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400
```

```
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
            485                 490                 495
Asn Ser Cys Lys Ala Thr Gly Gln Val Cys His Ala Leu Cys Ser Pro
        500                 505                 510
Glu Gly Cys Trp Gly Pro Glu Pro Arg Asp Cys Val Ser Cys Arg Asn
    515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
            565                 570                 575
Asp Asn Cys Ile Gln Cys Ala His Tyr Ile Asp Gly Pro His Cys Val
        580                 585                 590
Lys Thr Cys Pro Ala Gly Val Met Gly Glu Asn Asn Thr Leu Val Trp
    595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
            645                 650                 655
Leu Leu Val Val Ala Leu Gly Ile Gly Leu Phe Met Arg Arg Arg His
        660                 665                 670
Ile Val Arg Lys Arg Thr Leu Arg Arg Leu Leu Gln Glu Arg Glu Leu
    675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
            725                 730                 735
Lys Val Lys Ile Pro Val Ala Ile Lys Glu Leu Arg Glu Ala Thr Ser
        740                 745                 750
Pro Lys Ala Asn Lys Glu Ile Leu Asp Glu Ala Tyr Val Met Ala Ser
    755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
            805                 810                 815
Trp Cys Val Gln Ile Ala Lys Gly Met Asn Tyr Leu Glu Asp Arg Arg
```

```
                   820                825                830
Leu Val His Arg Asp Leu Ala Ala Arg Asn Val Leu Lys Thr Pro
               835                840                845
Gln His Val Lys Ile Thr Asp Phe Gly Leu Ala Lys Leu Leu Gly Ala
           850                855                860
Glu Lys Glu Tyr His Ala Glu Gly Gly Lys Val Pro Ile Lys Trp
865                870                875                880
Met Ala Leu Glu Ser Ile Leu His Arg Ile Tyr Thr His Gln Ser Asp
               885                890                895
Val Trp Ser Tyr Gly Val Thr Val Trp Glu Leu Met Thr Phe Gly Ser
               900                905                910
Lys Pro Tyr Asp Gly Ile Pro Ala Ser Glu Ile Ser Ser Ile Leu Glu
               915                920                925
Lys Gly Glu Arg Leu Pro Gln Pro Pro Ile Cys Thr Ile Asp Val Tyr
               930                935                940
Met Ile Met Val Lys Cys Trp Met Ile Asp Ala Asp Ser Arg Pro Lys
945                950                955                960
Phe Arg Glu Leu Ile Ile Glu Phe Ser Lys Met Ala Arg Asp Pro Gln
               965                970                975
Arg Tyr Leu Val Ile Gln Gly Asp Glu Arg Met His Leu Pro Ser Pro
               980                985                990
Thr Asp Ser Asn Phe Tyr Arg Ala Leu Met Asp Glu Glu Asp Met Asp
               995                1000                1005
Asp Val Val Asp Ala Asp Glu Tyr Leu Ile Pro Gln Gln Gly Phe
           1010                1015                1020
Phe Ser Pro Ser Thr Ser Arg Thr Pro Leu Leu Ser Ser Leu
       1025                1030                1035
Ser Ala Thr Ser Asn Asn Ser Thr Val Ala Cys Ile Asp Arg Asn
       1040                1045                1050
Gly Leu Gln Ser Cys Pro Ile Lys Glu Asp Ser Phe Leu Gln Arg
       1055                1060                1065
Tyr Ser Ser Asp Pro Thr Gly Ala Leu Thr Glu Asp Ser Ile Asp
       1070                1075                1080
Asp Thr Phe Leu Pro Val Pro Glu Tyr Ile Asn Gln Ser Val Pro
       1085                1090                1095
Lys Arg Pro Ala Gly Ser Val Gln Asn Pro Val Tyr His Asn Gln
       1100                1105                1110
Pro Leu Asn Pro Ala Pro Ser Arg Asp Pro His Tyr Gln Asp Pro
       1115                1120                1125
His Ser Thr Ala Val Gly Asn Pro Glu Tyr Leu Asn Thr Val Gln
       1130                1135                1140
Pro Thr Cys Val Asn Ser Thr Phe Asp Ser Pro Ala His Trp Ala
       1145                1150                1155
Gln Lys Gly Ser His Gln Ile Ser Leu Asp Asn Pro Asp Tyr Gln
       1160                1165                1170
Gln Asp Phe Phe Pro Lys Glu Ala Lys Pro Asn Gly Ile Phe Lys
       1175                1180                1185
Gly Ser Thr Ala Glu Asn Ala Glu Tyr Leu Arg Val Ala Pro Gln
       1190                1195                1200
Ser Ser Glu Phe Ile Gly Ala
       1205                1210
```

```
<210> SEQ ID NO 20
<211> LENGTH: 120
<212> TYPE: PRT
<213> ORGANISM: Artificial
<220> FEATURE:
<223> OTHER INFORMATION: heavy chain variable domain VH of anti-HER1
      antibody GA201

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
            115                 120

<210> SEQ ID NO 21
<211> LENGTH: 108
<212> TYPE: PRT
<213> ORGANISM: Artificial
<220> FEATURE:
<223> OTHER INFORMATION: light chain variable domain VL of anti-HER1
      antibody GA201

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr
            100                 105
```

COMBINATION THERAPY OF ANTI-HER3 ANTIBODIES

CROSS REFERENCE TO RELATED APPLICATIONS

This application claims priority to European Patent Application No. EP 13151076.0 filed Jan. 11, 2013, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Jan. 7, 2014, is named P5733US_ST25.txt and is 54,072 bytes in size.

FIELD OF THE INVENTION

The present invention relates to the combination therapy of anti-HER3 antibodies with certain anti-HER antibodies.

BACKGROUND OF THE INVENTION

Human HER3 (ErbB-3, ERBB3, c-erbB-3,c-erbB3, receptor tyrosine-protein kinase erbB-3, SEQ ID NO: 17) encodes a member of the epidermal growth factor receptor (EGFR) family of receptor tyrosine kinases which also includes HER1 (also known as EGFR), HER2, and HER4 (Kraus, M. H. et al, PNAS 86 (1989) 9193-9197; Plowman, G. D. et al, PNAS 87 (1990) 4905-4909; Kraus, M. H. et al, PNAS 90 (1993) 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound protein has HER3 a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski M. X., et al, J. Biol. Chem. 269 (1994) 14661-14665; Alimandi M, et al, Oncogene. 10 (1995) 1813-1821; Hellyer, N. J., J. Biol. Chem. 276 (2001) 42153-4261; Singer, E., J. Biol. Chem. 276 (2001) 44266-44274; Schaefer, K. L., Neoplasia 8 (2006) 613-622).

Expression of this gene and/or expression of its protein have been reported in numerous cancers, including prostate, bladder, and breast tumors. Alternate transcriptional splice variants encoding different isoforms have been characterized. One isoform lacks the intermembrane region and is secreted outside the cell. This form acts to modulate the activity of the membrane-bound form. Additional splice variants have also been reported, but they have not been thoroughly characterized.

WO 97/35885 relates to HER3 antibodies. WO 2003/013602 relates to inhibitors of HER activity, including HER antibodies. WO 2007/077028, WO 2008/100624, WO2011076683, WO2011044311, WO2011136911, WO2012019024, WO2012022814, WO2012031198, WO2012044612, WO2012052230, WO2012059858 relate to HER3 antibodies.

Human HER2 refers to 185-kDa growth factor receptor also referred to as neu and c-erbB-2 (Slamon, et al., Science 235 (1987) 177-182; Swiss-Prot P04626) whose function is related to neoplastic transformation in human breast cancer cells. Overexpression of this protein has been identified in 20-30% of breast cancer patients where it correlates with regionally advanced disease, increased probability of tumor recurrence, and reduced patient survival. As many as 30-40% of patients having gastric, endometrial, salivary gland, non-small cell lung, pancreatic, ovarian, peritoneal, prostate, or colorectal cancers may also exhibit overexpression of this protein.

The HER receptor will generally comprise an extracellular domain, which may bind an HER ligand; a lipophilic transmembrane domain, a conserved intracellular tyrosine kinase domain, and a carboxyl-terminal signaling domain harboring several tyrosine residues which can be phosphorylated. The extracellular domain of HER2 comprises four domains, Domain I (amino acid residues from about 1-195), Domain II (amino acid residues from about 196-320), Domain III (amino acid residues from about 321 488), and Domain IV (amino acid residues from about 489-632) (residue numbering without signal peptide). See Garrett, et al., Mol. Cell. 11 (2003) 495-505, Cho, et al., Nature 421 (2003) 756-760, Franklin, et al., Cancer Cell 5 (2004) 317-328, or Plowman, et al., Proc. Natl. Acad. Sci. 90 (1993) 1746-1750 and WO 2006/007398.

Trastuzumab (sold under the tradename Herceptin®) is a recombinant humanized anti-HER2 monoclonal antibody used for the treatment of HER2 over-expressed/HER2 gene amplified metastatic breast cancer. Trastuzumab binds specifically to the same epitope of HER2 as the murine anti-HER2 antibody 4D5 described in Hudziak, et al., Mol. Cell. Biol. 9 (1989) 1165-1172. Trastuzumab is a recombinant humanized version of the murine anti-HER2 antibody 4D5, referred to as rhuMAb 4D5 or trastuzumab) and has been clinically active in patients with HER2-overexpressing metastatic breast cancers that had received extensive prior anticancer therapy. (Baselga, et al, J. Clin. Oncol. 14 (1996) 737-744). Trastuzumab and its method of preparation are described in U.S. Pat. No. 5,821,337.

Pertuzumab (Omnitarg®) is another recombinant humanized anti-HER2 monoclonal antibody used for the treatment of HER2 positive cancers. Pertuzumab binds specifically to the 2C4 epitope, a different epitope on the extracellular domain of HER2 as trastuzumab. Pertuzumab is the first in a new class of HER2 dimerisation inhibitors (HDIs). Through its binding to the HER2 extracellular domain, pertuzumab inhibits dimerization of HER2 (with other HER family members), thereby inhibiting downstream signalling pathways and cellular processes associated with tumour growth and progression (Franklin, M. C., et al. Cancer Cell 5 (2004) 317-328 and Friess, T, et al. Clin Cancer Res 11 (2005) 5300-5309). Pertuzumab is a recombinant humanized version of the murine anti-HER2 antibody 2C4 (referred to as rhuMAb 2C4 or pertuzumab) and it is described together with the respective method of preparation in WO 01/00245 and WO 2006/007398.

The "epitope 2C4" is the region in the extracellular domain of HER2 to which the antibody 2C4 binds. In order to screen for antibodies which bind to the 2C4 epitope, a routine cross-blocking assay such as that described in "Ed. Harlow and David Lane, Antibodies, A Laboratory Manual, Cold Spring Harbor Laboratory, (1988)", can be performed. Alternatively, epitope mapping can be performed to assess whether the antibody binds to the 2C4 epitope of HER2 (e.g. any one or more residues in the region from about residue 22 to about residue 584 of HER2, inclusive). Epitope 2C4 comprises residues from domain II in the extracellular domain of HER2. 2C4 and pertuzumab bind to the extracellular domain of HER2 at the junction of domains I, II and III. See also Franklin, et al., Cancer Cell 5 (2004) 317-328.

Human HER1 (also known as r Erb-B1 or Human epidermal growth factor receptor (EGFR) (SEQ ID NO: 19) is a 170 kDa transmembrane receptor encoded by the c-erbB proto-oncogene, and exhibits intrinsic tyrosine kinase activity (Modjtahedi, H., et al., Br. J. Cancer 73 (1996) 228-235; Herbst, R. S., and Shin, D. M., Cancer 94 (2002) 1593-1611). SwissProt database entry P00533 provides the sequence of EGFR. There are also isoforms and variants of EGFR (e.g., alternative RNA transcripts, truncated versions, polymorphisms, etc.) including but not limited to those identified by Swissprot database entry numbers P00533-1, P00533-2, P00533-3, and P00533-4. EGFR is known to bind ligands including epidermal growth factor (EGF), transforming growth factor-α (TGf-α), amphiregulin, heparin-binding EGF (hb-EGF), betacellulin, and epiregulin (Herbst, R. S., and Shin, D. M., Cancer 94 (2002) 1593-1611; Mendelsohn, J., and Baselga, J., Oncogene 19 (2000) 6550-6565). EGFR regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay, G., et al., Ann. Oncology 14 (2003) 1346-1363; Tsao, A. S., and Herbst, R. S., Signal 4 (2003) 4-9; Herbst, R. S., and Shin, D. M., Cancer 94 (2002) 1593-1611; Modjtahedi, H., et al., Br. J. Cancer 73 (1996) 228-235).

Overexpression of HER1 has been reported in numerous human malignant conditions, including cancers of the bladder, brain, head and neck, pancreas, lung, breast, ovary, colon, prostate, and kidney. (Atalay, G., et al., Ann. Oncology 14 (2003) 1346-1363; Herbst, R. S., and Shin, D. M., Cancer 94 (2002) 1593-1611; Modjtahedi, H., et al., Br. J. Cancer 73 (1996) 228-235). In many of these conditions, the overexpression of EGFR correlates or is associated with poor prognosis of the patients. (Herbst R. S., and Shin, D. M., Cancer 94 (2002) 1593-1611; Modjtahedi, H., et al., Br. J. Cancer 73 (1996) 228-235). HER1 is also expressed in the cells of normal tissues, particularly the epithelial tissues of the skin, liver, and gastrointestinal tract, although at generally lower levels than in malignant cells (Herbst, R. S., and Shin, D. M., Cancer 94 (2002) 1593-1611).

WO 2006/082515 refers to humanized anti-EGFR monoclonal antibodies derived from the rat monoclonal antibody ICR62 and to their glycoengineered forms for cancer therapy.

SUMMARY OF THE INVENTION

The invention provides a combination therapy of an anti-HER3 antibody with an antibody which binds to human HER2 and which inhibits dimerization of HER2, or with an antibody which binds to HER1, wherein the antibody which binds to human HER1, is characterized in being glycosylated with a sugar chain at Asn297 whereby the amount of fucose within said sugar chain is 65% or lower. In one embodiment the antibody which binds to human HER3 is further characterized in that is glycosylated with a sugar chain at Asn297 whereby the amount of fucose within said sugar chain is 65% or lower.

In one aspect of the invention is an antibody which binds to human HER3 for use in the treatment of cancer in combination with an antibody which binds to human HER2 and which inhibits dimerization of HER2, wherein the cancer is a HER2-normal cancer.

In one embodiment the antibody which binds to human HER3 is characterized in that the heavy chain variable domain comprises a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6 or a CDR1L region of SEQ ID NO:7.

In one embodiment the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.

In one embodiment the antibody which binds to human HER3 is characterized in that
the heavy chain variable domain VH is SEQ ID NO:8; and
the light chain variable domain VL is SEQ ID NO:10.

In one embodiment the antibody which binds to human HER3 described above is further characterized in that is glycosylated with a sugar chain at Asn297 whereby the amount of fucose within said sugar chain is 65% or lower.

In one embodiment the antibody which binds to human HER2 and which inhibits dimerization of HER2 is pertuzumab.

In one embodiment the cancer is characterized by a HER3 expression.

In one embodiment the cancer is breast cancer, ovarian cancer, gastric cancer, prostate cancer, pancreatic cancer or cancer of the head or neck breast cancer.

Surprisingly it was found that the combination therapy an anti-HER3 antibody described above with an antibody which binds to human HER2 and which inhibits dimerization of HER2 showed strong tumor growth inhibition of HER2 normal expressing cancers, even in tumors where the an antibody which binds to human HER2 and which inhibits dimerization of HER2, only showed low to medium tumor growth inhibition when administered alone.

Another aspect of the invention is an antibody which binds to human HER3 for use in the treatment of cancer in combination with an antibody which binds to human HER1, wherein at least one of the antibody which binds to human HER3 and the antibody which binds to human HER1 is characterized in that the antibody is glycosylated with a sugar chain at Asn297 whereby the amount of fucose within said sugar chain is 65% or lower.

In one embodiment, both, the antibody which binds to human HER3 and the antibody which binds to human HER1, are characterized in being glycosylated with a sugar chain at Asn297 whereby the amount of fucose within said sugar chain is 65% or lower.

In one embodiment the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.

In one embodiment the antibody which binds to human HER3 is characterized in that the heavy chain variable domain VH is SEQ ID NO:8; and the light chain variable domain VL is SEQ ID NO:10.

In one embodiment the antibody which binds to human HER1 is characterized in that the heavy chain variable domain VH is SEQ ID NO:20; and the light chain variable domain VL is SEQ ID NO:21.

In one embodiment the cancer is characterized by a HER3 expression.

In one embodiment the cancer is further characterized by a HER1 expression.

In one embodiment the cancer is lung cancer or breast cancer, colorectal cancer, or head and neck cancer (in one embodiment characterized by a HER3 and HER1 expression).

Surprisingly it was found that the combination therapy an anti-HER3 antibody described above with an antibody which binds to human HER1 wherein at least one of the antibody which binds to human HER3 and the antibody which binds to human HER1 is characterized in that the antibody is glycosylated with a sugar chain at Asn297 whereby the amount of fucose within said sugar chain is 65% or lower, showed strong tumor growth inhibition, even in tumors where the antibody which binds to human HER1 only showed low to medium tumor growth inhibition when administered alone.

DESCRIPTION OF THE FIGURES

FIG. 7C) and with pertuzumab (anti-HER2) in an s.c. patient-derived breast cancer tumor xenografts model MAXF 449 (FIG. 7D).

DETAILED DESCRIPTION OF THE INVENTION

Figure 1B:
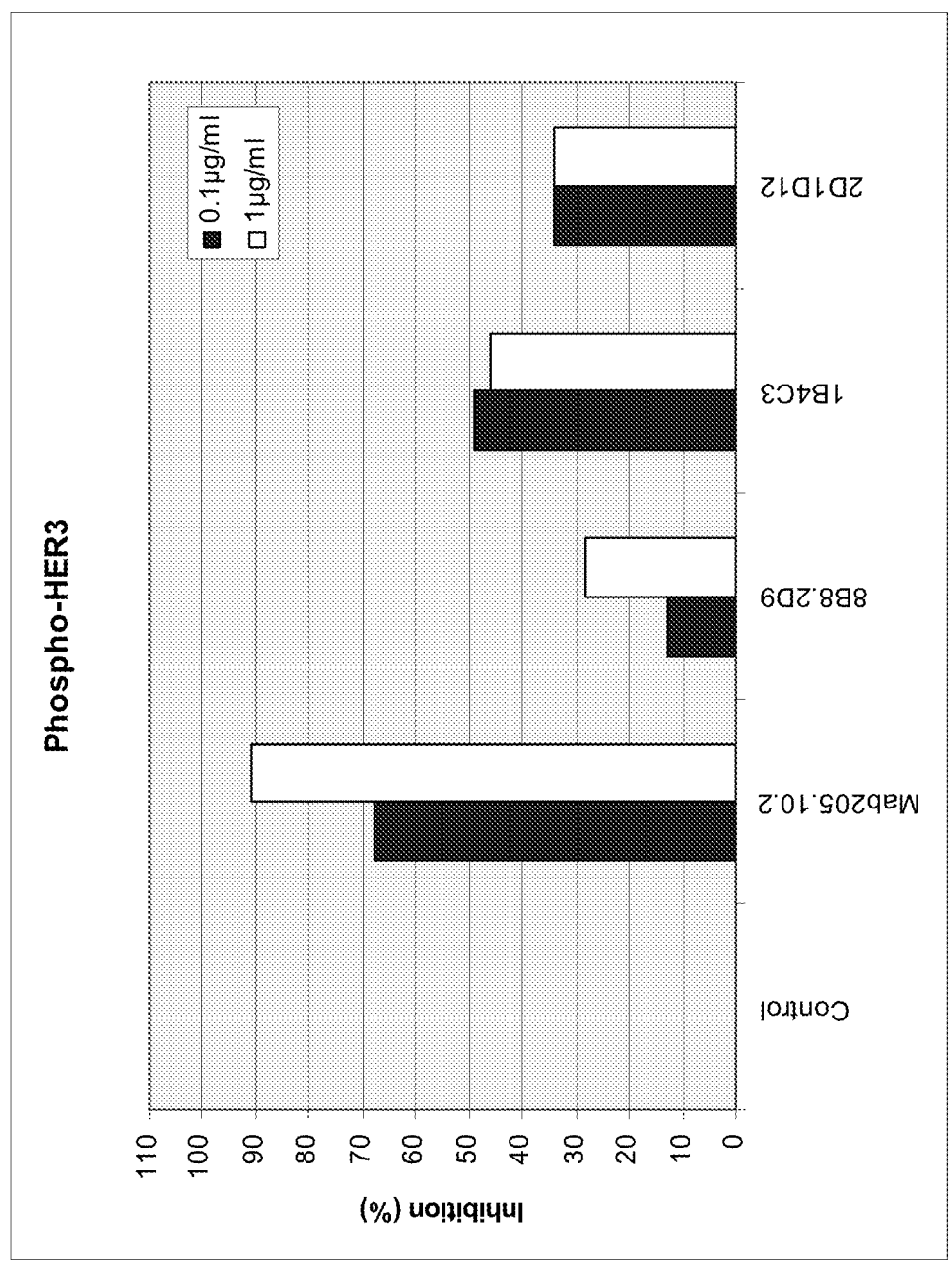
FIGS. 1A and B: Percent (%) inhibition of anti-HER3 antibodies on receptor phosphorylation in MCF7 cells in different concentrations.
FIG. 1C Percent (%) inhibition of anti-HER3 antibodies on receptor phosphorylation in Mel-Juso cells in different concentrations.

The invention comprises an antibody which binds to human HER3, characterized in that the heavy chain variable domain comprises a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6 or a CDR1L region of SEQ ID NO:7 for use in the combination therapies described herein.

The invention further comprises an antibody according to the invention characterized in that the heavy chain variable domain VH is SEQ ID NO:8; and the light chain variable domain VL is SEQ ID NO:9, or the light chain variable domain VL is SEQ ID NO:10, or the light chain variable domain VL is SEQ ID NO:11; or a humanized version thereof for use in the combination therapies described herein.

The invention further comprises an antibody according to the invention characterized in that the heavy chain variable domain VH is SEQ ID NO:8; and the light chain variable domain VL is SEQ ID NO:9, or the light chain variable domain VL is SEQ ID NO:10, or the light chain variable domain VL is SEQ ID NO:11 for use in the combination therapies described herein.

In one embodiment the antibody according to the invention is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6 for use in the combination therapies described herein.

In one embodiment the antibody according to the invention is characterized in that the heavy chain variable domain VH is SEQ ID NO:8; and the light chain variable domain VL is SEQ ID NO:9 or the light chain variable domain VL is SEQ ID NO:11 for use in the combination therapies described herein.

In one embodiment the antibody according to the invention is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7 for use in the combination therapies described herein.

In one embodiment the antibody according to the invention is characterized in that the heavy chain variable domain VH is SEQ ID NO:8; and the light chain variable domain VL is SEQ ID NO:10 for use in the combination therapies described herein.

In one embodiment such antibody is monoclonal. In one embodiment such antibody is humanized or human. In one embodiment such antibody is of IgG1 or IgG4 subclass. In one embodiment such antibody is a monoclonal humanized antibody of IgG1 subclass. In one embodiment such antibody is characterized in that said antibody is glycosylated with a sugar chain at Asn297 whereby the amount of fucose within said sugar chain is 65% or lower.

The invention comprises the humanized antibodies Mab 205.10.1, Mab 205.10.2 and Mab 205.10.3 with their respective VH and VL or CDRs for use in the combination therapies described herein.

| Antibody | VH | VL |
|---|---|---|
| Mab 205.10.1 | SEQ ID NO: 8 | SEQ ID NO: 9 |
| Mab 205.10.2 | SEQ ID NO: 8 | SEQ ID NO: 10 |
| Mab 205.10.3 | SEQ ID NO: 8 | SEQ ID NO: 11 |

| Antibody | CDR3H | CDR2H | CDR1H | CDR3L | CDR2L | CDR1L |
|---|---|---|---|---|---|---|
| Mab 205.10.1 | SEQ ID NO: 1 | SEQ ID NO: 2 | SEQ ID NO: 3 | SEQ ID NO: 4 | SEQ ID NO: 5 | SEQ ID NO: 6 |
| Mab 205.10.2 | SEQ ID NO: 1 | SEQ ID NO: 2 | SEQ ID NO: 3 | SEQ ID NO: 4 | SEQ ID NO: 5 | SEQ ID NO: 7 |
| Mab 205.10.3 | SEQ ID NO: 1 | SEQ ID NO: 2 | SEQ ID NO: 3 | SEQ ID NO: 4 | SEQ ID NO: 5 | SEQ ID NO: 6 |

In one embodiment such antibodies comprise constant regions of human origin e.g. SEQ ID NO:12-16, preferably of SEQ ID NO:12-13.

The term "antibody" encompasses the various forms of antibody structures including, but not being limited to, whole antibodies and antibody fragments. The antibody according to the invention is preferably a human antibody, humanized antibody, chimeric antibody, or further genetically engineered antibody as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to the respective antigen being able to assemble together with a $V_H$ domain to a functional antigen binding site and thereby providing the properties of an antibody according to the invention.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising a mouse variable region and a human constant region are especially preferred. Such rat/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. No. 5,202,238 and U.S. Pat. No. 5,204,244.

The term "humanized antibody" or "humanized version of an antibody" refers to antibodies in which the framework or "complementarity determining regions" (CDR) have been modified to comprise the CDR of an immunoglobulin of different specificity as compared to that of the parent immunoglobulin. In a preferred embodiment, the CDRs of the VH and VL are grafted into the framework region of human antibody to prepare the "humanized antibody." See e.g. Riechmann, L., et al., Nature 332 (1988) 323-327; and Neuberger, M. S., et al., Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix 1P A.1P.1-A.1P.37 and are accessible via IMGT, the international ImMunoGeneTics information System®. Optionally the framework region can be modified by further mutations. Particularly preferred CDRs correspond to those representing sequences recognizing the antigens noted above for chimeric antibodies. Preferably such humanized version is chimerized with a human constant region (see e.g. Sequences SEQ ID NO:12-16). The term "humanized antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M. D., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. L., p. 77 (1985); and Boerner, P., et al., J. Immunol. 147 (1991) 86-95). As already mentioned for and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

As used herein, the terms "which binds to human HER3", "which specifically binds to human HER3", or "anti-HER3 antibody" are interchangeable and refer to an antibody which specifically binds to the human HER3 antigen with a binding affinity of KD-value of $1.0 \times 10^{-8}$ mol/l or lower at 25° C., in one embodiment of a KD-value of $1.0 \times 10^{-9}$ mol/l or lower at 25° C. The binding affinity is determined with a standard binding assay at 25° C., such as surface plasmon resonance technique (BIAcore®, GE-Healthcare Uppsala, Sweden). A method for determining the KD-value of the binding affinity is described in Example 2b). Thus an "antibody which binds to human HER3" as used herein refers to an antibody specifically which binds to the human HER3 antigen with a binding affinity of KD $1.0 \times 10^{-8}$ mol/l or lower (in one embodiment of KD $1.0 \times 10^{-8}$ mol/l-$1.0 \times 10^{-13}$ mol/l) at 25° C.

As used herein, the terms "which binds to human HER2", "which specifically binds to human HER2", or "anti-HER2 antibody" are interchangeable and refer to an antibody which specifically binds to the human HER2 antigen with a binding affinity of KD-value of $1.0 \times 10^{-8}$ mol/l or lower at 25° C., in one embodiment of a KD-value of $1.0 \times 10^{-9}$ mol/l or lower at 25° C. The binding affinity is determined with a standard binding assay at 25° C., such as surface plasmon resonance technique (BIAcore®, GE-Healthcare Uppsala, Sweden). A method for determining the KD-value of the binding affinity is described in Example 2b). Thus an "antibody which binds to human HER2" as used herein refers to an antibody specifically which binds to the human HER2 antigen with a binding affinity of KD $1.0 \times 10^{-8}$ mol/l or lower (in one embodiment of KD $1.0 \times 10^{-8}$ mol/l-$1.0 \times 10^{-13}$ mol/l) at 25° C.

The pairing of HER receptors on the cell surface is referred to as dimerization. HER2 dimerizes with the other members of the HER family, including HER1, HER3, and HER4; HER2:HER3 dimerization is believed to produce the strongest mitogenic signaling and activate 2 key pathways that regulate cell survival and growth (Mitogen-activated protein kinase (MAPK) pathway and Phosphoinositide 3-kinase (PI3K) pathway). As used herein, the term "an antibody which binds to human HER2 and which inhibits dimerization of HER2" refer to an anti-HER2 antibody which specifically binds to the human HER2 antigen and which inhibits/blocks ligand-dependent HER2 heterodimerization with HER1, HER3, and HER4, and especially inhibits HER2/HER3 dimerization (see e.g. PERJETA Prescribing Information. Genentech, Inc. June 2012. Baselga J, et al; N Engl J. Med. 2012; 366:109-119; Baselga J, et al Nat Rev Cancer. 2009; 9:463-475; Hynes N E, et al Nat Rev Cancer. 2005; 5:341-354; Yarden Y, et al, Nat Rev Mol Cell Biol. 2001; 2:127-137; Hsieh A C, et al, Br J. Cancer. 2007; 97:453-457; Soltoff S P, et al, Mol Cell Biol. 1994; 14:3550-3558). Examples of such anti-HER2 antibodies which inhibit HER2 dimerization are described e.g. in WO 01/00245 and WO 2006/007398 wherein pertuzumab (referred to as rhuMAb 2C4 or pertuzumab) is described as one example.

As used herein, the terms "which binds to human HER1", "which specifically binds to human HER1", or "anti-HER1 antibody" are interchangeable and refer to an antibody which specifically binds to the human HER2 antigen with a binding affinity of KD-value of $1.0 \times 10^{-8}$ mol/l or lower at 25° C., in one embodiment of a KD-value of $1.0 \times 10^{-9}$ mol/l or lower at 25° C. The binding affinity is determined with a standard binding assay at 25° C., such as surface plasmon resonance technique (BIAcore®, GE-Healthcare Uppsala, Sweden). A method for determining the KD-value of the binding affinity is described in Example 2b). Thus an "antibody which binds to human HER2" as used herein refers to an antibody specifically which binds to the human HER2 antigen with a binding affinity of KD $1.0 \times 10^{-8}$ mol/l or lower (in one embodiment of KD $1.0 \times 10^{-8}$ mol/l-$1.0 \times 10^{-13}$ mol/l) at 25° C.

Human HER3 (ErbB-3, ERBB3, c-erbB-3,c-erbB3, receptor tyrosine-protein kinase erbB-3, SEQ ID NO: 17 including signal peptide) encodes a member of the epidermal growth factor receptor (EGFR) family of receptor tyrosine kinases which also includes HER1 (also known as EGFR), HER2, and HER4 (Kraus, M. H. et al, PNAS 86 (1989), 9193-9197; Plowman, G. D. et al, PNAS 87 (1990), 4905-4909; Kraus, M. H. et al, PNAS 90 (1993), 2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase domain (TKD) and a C-terminal phosphorylation domain. This membrane-bound protein has HER3 a Heregulin (HRG) binding domain within the extracellular domain but not an active kinase domain. It therefore can bind this ligand but not convey the signal into the cell through protein phosphorylation. However, it does form heterodimers with other HER family members which do have kinase activity. Heterodimerization leads to the activation of the receptor-mediated signaling pathway and transphosphorylation of its intracellular domain. Dimer formation between HER family members expands the signaling potential of HER3 and is a means not only for signal diversification but also signal amplification. For example the HER2/HER3 heterodimer induces one of the most important mitogenic signals via the PI3K and AKT pathway among HER family members (Sliwkowski, M. X., et al, J. Biol. Chem. 269 (1994) 14661-14665; Alimandi, M., et al, Oncogene 10 (1995) 1813-1821; Hellyer, N. J., J. Biol. Chem. 276 (2001) 42153-421561; Singer, E., J. Biol. Chem. 276 (2001) 44266-44274; Schaefer, K. L., Neoplasia 8 (2006) 613-622).

HER3 antibodies Mab205.10.1, Mab205.10.2, and Mab205.10.3 showed a competitive binding with the ligand Heregulin (HRG) to HER3.

Expression of this gene and/or expression of its protein have been reported in numerous cancers, including prostate, bladder, and breast tumors. Alternate transcriptional splice variants encoding different isoforms have been characterized. One isoform lacks the intermembrane region and is secreted outside the cell. This form acts to modulate the activity of the membrane-bound form. Additional splice variants have also been reported, but they have not been thoroughly characterized.

The term "human HER2" according to the invention refers to 185-kDa growth factor receptor also referred to as neu and c-erbB-2 (Slamon, et al., Science 235 (1987) 177-182; Swiss-Prot P04626; SEQ ID NO:18 including signal peptide) whose function is related to neoplastic transformation in human breast cancer cells. The HER receptor will generally comprise an extracellular domain, which may bind an HER ligand; a lipophilic transmembrane domain, a conserved intracellular tyrosine kinase domain, and a carboxyl-terminal signaling domain harboring several tyrosine residues which can be phosphorylated. The extracellular domain of HER2 comprises four domains, Domain I (amino acid residues from about 1-195), Domain II (amino acid residues from about 196-320), Domain III (amino acid residues from about 321 488), and Domain IV (amino acid residues from about 489-632) (residue numbering without signal peptide). See Garrett, et al., Mol. Cell. 11 (2003) 495-505, Cho, et al., Nature 421 (2003) 756-760, Franklin, et al., Cancer Cell 5 (2004) 317-328, or Plowman, et al., Proc. Natl. Acad. Sci. 90 (1993) 1746-1750 and WO 2006/007398.

Pertuzumab (Omnitarg®) is another recombinant humanized anti-HER2 monoclonal antibody used for the treatment of HER2 positive cancers. Pertuzumab binds specifically to the 2C4 epitope, a different epitope on the extracellular domain of HER2 as trastuzumab. Pertuzumab is the first in a new class of HER dimerisation inhibitors (HDIs). Through its binding to the HER2 extracellular domain, pertuzumab inhibits dimerization of HER2 (especially ligand-activated heterodimerization with other HER family members), thereby inhibiting downstream signalling pathways and cellular processes associated with tumour growth and progression (Franklin, M. C., et al. Cancer Cell 5 (2004) 317-328 and Friess, T, et al. Clin Cancer Res 11 (2005) 5300-5309). Pertuzumab is a recombinant humanized version of the murine anti-HER2 antibody 2C4 (referred to as rhuMAb 2C4 or pertuzumab) and it is described together with the respective method of preparation in WO 01/00245 and WO 2006/007398.

The "epitope 2C4" is the region in the extracellular domain of HER2 to which the antibody 2C4 binds. In order to screen for antibodies which bind to the 2C4 epitope, a routine cross-blocking assay such as that described in "Ed. Harlow and David Lane, Antibodies, A Laboratory Manual, Cold Spring Harbor Laboratory, (1988)", can be performed. Alternatively, epitope mapping can be performed to assess whether the antibody binds to the 2C4 epitope of HER2 (e.g. any one or more residues in the region from about residue 22 to about residue 584 of HER2, inclusive). Epitope 2C4 comprises residues from domain II in the extracellular domain of HER2. 2C4 and pertuzumab bind to the extracellular domain of HER2 at the junction of domains I, II and III. See also Franklin, et al., Cancer Cell 5 (2004) 317-328.

The term "human HER1" (also known as r Erb-B1 or Human epidermal growth factor receptor (EGFR) (SEQ ID NO:19 including signal peptide)) is a 170 kDa transmembrane receptor encoded by the c-erbB proto-oncogene, and exhibits intrinsic tyrosine kinase activity (Modjtahedi, H., et al., Br. J. Cancer 73 (1996) 228-235; Herbst, R. S., and Shin, D. M., Cancer 94 (2002) 1593-1611). SwissProt database entry P00533 provides the sequence of EGFR. There are also isoforms and variants of HER1 (e.g., alternative RNA transcripts, truncated versions, polymorphisms, etc.) including but not limited to those identified by Swissprot database entry numbers P00533-1, P00533-2, P00533-3, and P00533-4. HER1 is known to bind ligands including epidermal growth factor (EGF), transforming growth factor-α (TGf-α), amphiregulin, heparin-binding EGF (hb-EGF), betacellulin, and epiregulin (Herbst, R. S., and Shin, D. M., Cancer 94 (2002) 1593-1611; Mendelsohn, J., and Baselga, J., Oncogene 19 (2000) 6550-6565). HER1 regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay, G., et al., Ann. Oncology 14 (2003) 1346-1363; Tsao, A. S., and Herbst, R. S., Signal 4 (2003) 4-9; Herbst, R. S., and Shin, D. M., Cancer 94 (2002) 1593-1611; Modjtahedi, H., et al., Br. J. Cancer 73 (1996) 228-235).

WO 2006/082515 refers to humanized anti-HER1 monoclonal antibodies derived from the rat monoclonal antibody ICR62 and to their glycoengineered forms for cancer therapy. One examples of such humanized, glycoengineered antibodies derived from the rat monoclonal antibody ICR62 is GA201 (described in WO 2006/082515). GA201 is a glycoengineered anti-HER1 antibodies characterized in comprising as heavy chain variable domain VH the amino acid sequence of SEQ ID NO: 20 (heavy chain variable domain VH, humanized <EGFR>ICR62-I-HHD) and in comprising as light chain variable domain VL the amino acid sequence of SEQ ID NO: 21 (light chain variable domain VL, humanized <EGFR>ICR62-I-KC) and further characterized in that said antibody is glycosylated with a sugar chain at Asn297 whereby the amount of fucose within said sugar chain is 65% or lower.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The "variable domain of an antibody according to the invention" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". The term "antigen-binding portion" of an antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The term "CDRH1" denotes the CDR1 region of the heavy chain variable region calculated according to Kabat. CDRH2, CDRH3, CDRL1, CDRL2 and CDRL3 mean the respective regions from the heavy (H) or light (L) chain. The extent of CDR and framework regions (FRs) is determined by comparison to a compiled database of amino acid sequences in which those regions have been defined according to variability among the sequences according to Kabat et al, Sequences of Proteins of Immunological Interest, 5th Ed. Public Health Service, National Institutes of Health, Bethesda, Md. (1991).

The "Fc part" of an antibody is not involved directly in binding of an antibody to an antigen, but exhibit various effector functions. A "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called a, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such binding sites are known in the state of the art and described e.g. by Boackle, R. J., et al., Nature 282 (1979) 742-743, Lukas, T. J., et al., J. Immunol. 127 (1981) 2555-2560, Brunhouse, R., and Cebra, J. J., Mol. Immunol. 16 (1979) 907-917, Burton, D. R., et al., Nature 288 (1980) 338-344, Thommesen, J. E., et al., Mol. Immunol. 37 (2000) 995-1004, Idusogie, E. E., et al., J. Immunol. 164 (2000) 4178-4184, Hezareh, M., et al., J. Virology 75 (2001) 12161-12168, Morgan, A., et al., Immunology 86 (1995) 319-324, EP 0 307 434. Such binding sites are e.g. L234, L235, D270, N297, E318, K320, K322, P331 and P329 (numbering according to EU index of Kabat, E. A., see below). Antibodies of subclass IgG1, IgG2 and IgG3 usually show complement activation and C1q and C3 binding, whereas IgG4 do not activate the complement system and do not bind C1q and C3.

In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, e.g. a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). Preferred are the human heavy chain constant regions of SEQ ID NO: 13 (human IgG1 subclass), SEQ ID NO: 14 (human IgG1 subclass with mutations L234A and L235A).

In one embodiment the antibody according to the invention is of human IgG1 subclass or of human IgG3 subclass. In one embodiment the antibody according to the invention is of human IgG1 subclass.

In one embodiment the antibody according to the invention is characterized in that the constant chains are of human origin. Such constant chains are well known in the state of the art and e.g. described by Kabat, E. A., (see e.g. Johnson, G. and Wu, T. T., Nucleic Acids Res. 28 (2000) 214-218). For example, a useful human heavy chain constant region comprises an amino acid sequence of SEQ ID NO: 13. For example, a useful human light chain constant region comprises an amino acid sequence of a kappa-light chain constant region of SEQ ID NO:12.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The terms "nucleic acid" or "nucleic acid molecule", as used herein, are intended to include DNA molecules and RNA molecules. A nucleic acid molecule may be single-stranded or double-stranded, but preferably is double-stranded DNA. A nucleic acid is "operably linked" when it is placed into a functional relationship with another nucleic acid. For example, DNA for a presequence or secretory leader is operable linked to DNA for a polypeptide if it is expressed as a preprotein that participates in the secretion of the polypeptide; a promoter or enhancer is operable linked to a coding sequence if it affects the transcription of the sequence; or a ribosome binding site is operable linked to a coding sequence if it is positioned so as to facilitate translation. Generally, "operable linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice. As used herein, the expressions "cell", "cell line", and "cell culture" are used interchangeably and all such designations include progeny. Thus, the words "transformants" and "transformed cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The anti-HER3 antibody described herein is preferably characterized in that the constant chains are of human origin. Such constant chains are well known in the state of the art and described, e.g., by Kabat et al., Sequences of Proteins of Immunological Interest, 5th ed., Public Health Service, National Institutes of Health, Bethesda, Md. (1991). For example, a useful human light chain constant region comprises an amino acid sequence of a kappa-light chain constant region of SEQ ID NO:12. For example, useful human heavy chain constant region comprises SEQ ID NO:13 to 16.

In another aspect, an anti-HER3 antibody for the respective combination therapy is provided, wherein the antibody comprises a VH as in any of the embodiments provided above, and a VL as in any of the embodiments provided above. In one embodiment, the antibody comprises the VH and VL sequences in SEQ ID NO:8 and SEQ ID NO:10, respectively; and having one or more of the following properties (determined in assays as described in Example 3 and 2):

the anti-HER3 antibody inhibits the HER3 phosphorylation in tumor cells such as MCF7 cells, FaDu cells or Mel-Juso cell (in one embodiment the anti-HER3 antibody shows an inhibition of the HER3 phosphorylation in MCF7 cells of at least 80% (in one embodiment at least 90%) at a concentration of 1.0 μg/ml; in one embodiment the anti-HER3 antibody shows an inhibition of the HER3 phosphorylation in FaDu cells of at least 80% (in one embodiment at least 90%) at a concentration of 0.1 μg/ml; in one embodiment the anti-HER3 antibody shows an inhibition of the HER3 phosphorylation in Mel-Juso cells of at least 60% (in one embodiment at least 70%) at a concentration of 0.1 μg/ml)

the anti-HER3 antibody inhibits the AKT phosphorylation in tumor cells such as Mel-Juso cell (in one embodiment the anti-HER3 antibody inhibits the AKT phosphorylation in Mel-Juso cells with an IC50 value of less than 0.50 μg/ml, in one embodiment with IC50 value of less than 0.35 μg/ml)

the anti-HER3 antibody inhibits the proliferation of tumor cells such as MDA-MB-175 cells (in one embodiment the anti-HER3 antibody inhibits the proliferation of MDA-MB-175 cells with an IC50 value of less than 10 μg/ml)

the anti-HER3 antibody binds to HER3 with a KD value of less than $5.0 \times 10^{-9}$M, in one embodiment with a KD value of less than $3.0 \times 10^{-9}$M.

In another aspect, an anti-HER3 antibody for the respective combination therapy is a bispecific anti-HER3/anti-HER1 antibody as described in US 2010/0255010. In one embodiment, the bispecific anti-HER3/anti-HER1 antibody is characterized comprising by the characteristic amino acid sequences disclosed in US 2010/0255010, i.e. A) (a) HVR-H1 comprising the amino acid sequence of LSGDWIH; (b) HVR-H2 comprising the amino acid sequence of VGEISAAGGYTD; and (c) HVR-H3 comprising the amino acid sequence of ARESRVSFEAAMDY; and (d) HVR-L1 comprising the amino acid sequence of NIATDVA; (e) HVR-L2 comprising the amino acid sequence of SASF; and (f) HVR-L3 comprising the amino acid sequence of SEPEPYT, or B) (a) a heavy chain variable domain with the amino acid sequence of SEQ ID NO: 30 as disclosed in US2010/0255010; (b) a light chain variable domain with the amino acid sequence of SEQ ID NO: 29 as disclosed in US2010/0255010;

The term "antibody-dependent cellular cytotoxicity (ADCC)" refers to lysis of human target cells by an antibody according to the invention in the presence of effector cells. ADCC is measured preferably by the treatment of a preparation of HER3 expressing cells with an antibody according to the invention in the presence of effector cells such as freshly isolated PBMC or purified effector cells from buffy coats, like monocytes or natural killer (NK) cells or a permanently growing NK cell line.

Cell-mediated effector functions like ADCC of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umana, P., et al., Nature Biotechnol. 17 (1999) 176-180 and WO 99/54342 showed that overexpression in Chinese hamster ovary (CHO) cells of B(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies via glycoengineering are reported e.g. in WO 2005/044859, WO 2004/065540, WO2007/031875, Umana, P., et al., Nature Biotechnol. 17 (1999) 176-180, WO 99/154342, WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835 and WO 2000/061739 or e.g. in Niwa, R., et al., J. Immunol. Methods 306 (2005) 151-160; Shinkawa, T., et al, J Biol Chem, 278 (2003) 3466-3473; WO 03/055993 and US 2005/0249722.

In one embodiment of the invention, the antibody according to the invention is afucosylated which means the antibody is glycosylated (if it comprises an Fc part of IgG1 or IgG3 subclass) with a sugar chain at Asn297 whereby the amount of fucose within said sugar chain is 80% or lower (Numbering according to Kabat), e.g. between 80% and 1%. In another embodiment is the amount of fucose within said sugar chain is 65% or lower, in one embodiment between 5% and 65%, in one embodiment from 0% to 65%, and in one embodiment the amount of fucose within said sugar chain is 0%. Such antibodies are referred to in the following as "afucosylated antibodies" or "non-fucosylated antibodies". Such afucosylated antibodies show enhanced ADCC whereas other antibody properties remain substantially unaffected.

In a further embodiment the amount of N-glycolylneuraminic acid (NGNA) is 1% or less and/or the amount of N-terminal alpha-1,3-galactose is 1% or less within said sugar chain. The sugar chain show preferably the characteristics of N-linked glycans attached to Asn297 of an antibody recombinantly expressed in a CHO cell.

"Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300.

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolyl-neuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E., A., et al., Sequences of Proteins of Immunological Interest, 5th Ed. Public Health Service, National Institutes of Health, Bethesda, Md. (1991), and by Brueggemann, M., et al., J. Exp. Med. 166 (1987) 1351-1361; Love, T. W., et al., Methods Enzymol. 178 (1989) 515-527. These structures are designated as G0, G1 (α-1,6- or α-1,3-), or G2 glycan residues, depending from the amount of terminal Gal residues (Raju, T. S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry (e.g. in LC/MS system) and calculated as average value (see e.g WO 2008/077546). The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis). Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880. The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including, column chromatography and others well known in the art (see Ausubel, F., et al., ed. Current Protocols in Molecular Biology, Greene Publishing and Wiley Interscience, New York (1987)). Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199. Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells. Antibodies obtainable from said cell lines are preferred embodiments of the invention. Afocusylated antibodies are preferably prepared via glycoengineering as described above.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In one aspect of the invention the antibodies of the combination are administered as a pharmaceutical composition comprising the respective antibody. In another aspect, the present invention provides a composition, e.g. a pharmaceutical composition, containing an antibody according to the present invention, formulated together with a pharmaceutical carrier.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colorectal cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers.

Another aspect of the invention is an anti-HER3-antibody according to the invention for the treatment of cancer in combination with an antibody which binds to human HER2 and which inhibits dimerization of HER2, wherein the cancer is a HER2-normal cancer. Another aspect of the invention is the use of an antibody which binds to human HER3 for the manufacture of a medicament for the treatment of cancer in combination with an antibody which binds to human HER2 and which inhibits dimerization of HER2, wherein the cancer is a HER2-normal cancer. Another aspect of the invention is a method of treatment of a patient suffering from cancer by administering an anti-HER3-antibody antibody according to the invention to said patient in the need of such treatment in combination with an antibody which binds to human HER2 and which inhibits dimerization of HER2, wherein the cancer is a HER2-normal cancer. In one embodiment, a) the anti-HER3 antibody used in this combination is characterized in comprising as VH an amino acid sequence of SEQ ID NO:8 and an as VL an amino acid sequence of SEQ ID NO: 10, b) the anti-HER2 antibody used in this combination is pertzumab, and c) the cancer is breast cancer, ovarian cancer, gastric cancer, prostate cancer, pancreatic cancer or cancer of the head or neck (or in one embodiment breast cancer).

Another aspect of the invention is an anti-HER3 antibody according to the invention for the treatment of cancer in combination with an antibody which binds to human HER1 wherein both, the antibody which binds to human HER3 and the antibody which binds to human HER1, are characterized in being glycosylated with a sugar chain at Asn297 whereby the amount of fucose within said sugar chain is 65% or lower. Another aspect of the invention is the use of an antibody which binds to human HER3 for the manufacture of a medicament for the treatment of cancer in combination with an antibody which binds to human HER1 wherein both, the antibody which binds to human HER3 and the antibody which binds to human HER1, are characterized in being glycosylated with a sugar chain at Asn297 whereby the amount of fucose within said sugar chain is 65% or lower. Another aspect of the invention is a method of treatment of a patient suffering from cancer by administering an anti-HER3 antibody antibody according to the invention to said patient in the need of such treatment in combination with an antibody which binds to human HER1 wherein both, the antibody which binds to human HER3 and the antibody which binds to human HER1, are characterized in being glycosylated with a sugar chain at Asn297 whereby the amount of fucose within said sugar chain is 65% or lower. In one embodiment, a) the anti-HER3 antibody used in this combination is characterized in comprising as VH an amino acid sequence of SEQ ID NO:8 and an as VL an amino acid sequence of SEQ ID NO: 10, b) the anti-HER1 antibody used in this combination is characterized in comprising as VH an amino acid sequence of SEQ ID NO:20 and an as VL an amino acid sequence of SEQ ID NO: 21, and c) the cancer is lung cancer, breast cancer, colorectal cancer, or head and neck cancer.

In one preferred embodiment of the invention all such cancer mentioned above are further characterized by HER3 expression. HER3 expression refers to HER3 protein and/or gene expression (amplification). The expression level of HER3 may be detected by an immunohistochemical method, whereas said HER3 gene amplification status can be measured with in situ hybridization methods, like fluorescence in situ hybridization techniques (FISH). Corresponding assays and kits are well known in the art, for protein expression assays as well as for the detection of gene amplifications. Alternatively other methods like qRT-PCR might be used to detect levels of HER3 gene expression. The expression level of HER3 can, inter alia, be detected by an immunohistochemical method. Such methods are well known in the art (see e.g. analogous methods and test for HER2 expression levels below).

In one preferred embodiment the cancer is characterized by a high (increased) pHER3/HER3 ratio (analyzed by e.g. by IHC of fresh frozen tumor tissue; in preclinical setting Western blot Standard SDS-PAGE and Western blotting was performed using a phosphor-HER3 antibody (αPhospho-HER3 clone 21D3 [Tyr1289]; Cell Signaling Technologies, #4791) or anti-HER3 antibody (αHER3 clone C-17; Santa Cruz, #sc-285). E.g. Signal can be detected using electrochemiluminescence (Amersham, RPN2209) and percent inhibition of HER3 receptor phosphorylation calculated for each concentration of HER3 antibody is tested. For analysis of HER3 phosphorylation in tumors, tumor lysates are prepared and equal amounts (20 µg/lane) and are separated on SDS page. Western blotting for HER3 and phosphorylated HER3 (pHER3) is performed as above)

In the context of the combination therapy of HER3 antibody with anti-HER2 antibodies, which anti-HER2 antibodies inhibit HER2 dimerization, the term "HER2-normal cancer" as used herein refers to a cancer/tumorous tissue etc. which comprises cancer cells which have normal levels of HER2, meaning they don't have HER2 overexpression, as defined for HER2-positive cancer, or they are not negative for HER2 expression. For the purpose of the present invention, "HER2-normal cancer" has an immunohistochemistry (IHC) score of 2+ and an in situ hybridization (ISH) amplification ratio <2.0 (i.e. is ISH-negative) or an immunohistochemistry (IHC) score of 1+ and an in situ hybridization (ISH) amplification ratio <2.0 (i.e. is ISH-negative). Accordingly, HER2-normal cancer is present if a low (IHC 1+) or moderate (IHC 2+) HER2 (protein) expression level detected e.g. by immunohistochemical methods and no HER2 gene amplification, detected by in-situ-hybridization (ISH negative, like a HER2 gene copy <4 copies of the HER2 gene per tumor cell or ratio of <2.0 for the number of HER2 gene copies to the number of signals for CEP17.), is found in samples obtained from the patients such as breast tissue biopsies or breast tissue resections or in tissue derived from metastatic sites. In one embodiment "HER2-normal cancer" is defined as an immunohistochemistry (IHC) score of HER2(2+) and ISH negative or immunohistochemistry (IHC) score of HER2(1+) and ISH negative (IHC 1+/ISH-negative or IHC 2+/ISH-negative).

The expression level of HER2 may be detected by an immunohistochemical method, whereas said HER2 gene amplification status can be measured with in situ hybridization methods, like fluorescence in situ hybridization techniques (FISH). Corresponding assays and kits are well known in the art, for protein expression assays as well as for the detection of gene amplifications. Alternatively other methods like qRT-PCR might be used to detect levels of HER2 gene expression.

The expression level of HER2 can, inter alia, be detected by an immunohistochemical method. Such methods are well known in the art and corresponding commercial kits are available. Exemplary kits which may be used in accordance with the present invention are, inter alia, HercepTest™ produced and distributed by the company Dako or the test called Ventana Pathway™. The level of HER2 protein expression may be assessed by using the reagents provided with and following the protocol of the HercepTest™. A skilled person will be aware of further means and methods for determining the expression level of HER2 by immunohistochemical methods; see for example WO 2005/117553. Therefore, the expression level of HER2 can be easily and reproducibly determined by a person skilled in the art without undue burden. However, to ensure accurate and reproducible results, the testing must be performed in a specialized laboratory, which can ensure validation of the testing procedures.

The expression level of HER2 can be classified in a low expression level, an intermediate expression level and a high expression level. It is preferred in context of this invention that HER2-normal disease is defined by a low or weak expression level of HER2 (e.g. HER2(1+ or 2+) by IHC) and a negative ISH result, for example determined in a sample of a cancer patient. Therefore parallel testing using immunohistochemistry and in situ hybridisation is preferred.

The recommended scoring system to evaluate the IHC staining patterns in breast cancer which reflect the expression levels of HER2 designated herein HER2(0), HER2(+), HER2(++) and HER2(+++), is as follows:

The below IHC staining patterns are recommended for determining HER2 status in breast cancer (see Dako Herceptest package insert).

| Staining Intensity Score | Staining Pattern | HER2 over-expression assessment |
| --- | --- | --- |
| 0 | No staining is observed or membrane staining is observed in <10% of the tumor cells | negative |
| 1+ | A faint/barely perceptible membrane staining is detected in >10% of the tumor cells. The cells are only stained in part of their membrane. | negative |
| 2+ | A weak to moderate complete membrane staining is detected in >10% of the tumor cells. | weakly positive. |
| 3+ | A strong complete membrane staining is detected in >10% of the tumor cells. | strongly positive |

The above IHC staining patterns are routinely used in determining HER2 status in breast cancer. The terms HER2 (+), HER2(++) and HER2(+++) used herein are equivalent to the terms HER2(1+), HER2(2+) and HER2(3+). A "normal HER2 protein expression level" used in context of this invention corresponds to a 1+score ("negative assessment" according to the table shown herein above), and a 2+score "weakly positive". As described herein above in detail, the evaluation of the protein expression level (i.e. the scoring system as shown in the table) is based on results obtained by immunohistochemical methods. As a standard or routinely, the HER-2 status is, accordingly, performed by immunohistochemistry with one of two FDA-approved commercial kits available; namely the Dako Herceptest™ and the Ventana Pathway™. These are semi-quantitative assays which stratify expression levels into 0 (<20,000 receptors per cell, no expression visible by IHC staining), 1+ (~100,000 receptors per cell, partial membrane staining, <10% of cells overexpressing HER-2), 2+ (~500,000 receptors per cell, light to moderate complete membrane staining, >10% of cells overexpressing HER-2), and 3+ (~2,000,000 receptors per cell, strong complete membrane staining, >10% of cells overexpressing HER-2).

Alternatively, further methods for the evaluation of the protein expression level of HER2 may be used, e.g. Western Blots, ELISA-based detection systems and so on.

The below IHC staining patterns are recommended for determining HER2 status in gastric cancer (see Dako Herceptest package insert):

| Staining Intensity Score | Surgical specimen - staining pattern | Biopsy specimen - staining pattern | HER2 Overexpression Assessment |
| --- | --- | --- | --- |
| 0 | No reactivity or no membranous reactivity in <10% of tumour cells | No reactivity or no membranous reactivity in any tumour cell | Negative |
| 1+ | Faint/barely perceptible membranous reactivity in ≥10% of tumour cells; cells are reactive only in part of their membrane | Tumour cell cluster (≥5 cells) with a faint/barely perceptible membranous reactivity irrespective of percentage of tumour cells stained | Negative |
| 2+ | Weak to moderate complete, basolateral or lateral membranous reactivity in ≥10% of tumour cells | Tumour cell cluster (≥5 cells) with a weak to moderate complete, basolateral or lateral membranous reactivity irrespective of percentage of tumour cells stained | Equivocal |
| 3+ | Strong complete, basolateral or lateral membranous reactivity in ≥10% of tumour cells | Tumour cell cluster (≥5 cells) with a strong complete, basolateral or lateral membranous reactivity irrespective of percentage of tumour cells stained | Positive |

HER2-normal disease is defined by a low or weak expression level of HER2 (e.g. HER2(1+ or 2+) by IHC) and a negative ISH result.

In accordance with the above, the sample to be assessed can be (obtained) from a patient with HER2-normal cancer as defined above. For example, the sample may be obtained from a tumorous tissue, (a) tumor(s) and, accordingly, is (a) tumor cell(s) or (a) tumor tissue(s) suspected of being HER2 expressing tumour, like a breast tumor. A person skilled in the art is in the position to identify such tumors and/or individuals/patients suffering from corresponding cancer using standard techniques known in the art and methods disclosed herein. Generally, said tumor cell or cancer cell may be obtained from any biological source/organism, particularly any biological source/organism, suffering from the above-mentioned cancer. In context of this invention particular useful cells are, preferably, human cells. These cells can be obtained from e.g. biopsies or from biological samples. The tumor/cancer/tumor cell/cancer cell is a solid tumor/cancer/tumor cell/cancer cell. In accordance with the above, the cancer/tumor cell may be a breast cancer/tumor cell or said sample comprises a cancer/tumor cell, such as a breast cancer/tumor cell. In line with the above, said tumor/cancer may be a breast tumor/cancer.

In the context of the combination therapy of an anti-HER3 antibody with an anti-HER1 antibody, wherein both (or at least one), the antibody which binds to human HER3 and the antibody which binds to human HER1, are characterized in being glycosylated with a sugar chain at Asn297 whereby the amount of fucose within said sugar chain is 65% or lower, HER1 expression refers to HER1 protein and/or gene expression (amplification). The expression level of HER1 may be detected by an immunohistochemical method, whereas said HER1 gene amplification status can be measured with in situ hybridization methods, like fluorescence in situ hybridization techniques (FISH). Corresponding assays and kits are well known in the art, for protein expression assays as well as for the detection of gene amplifications. Alternatively other methods like qRT-PCR might be used to detect levels of HER1 gene expression. The expression level of HER1 can, inter alia, be detected by an immunohistochemical method. Such methods are well known in the art (see e.g. analogous methods and test for HER2 expression levels above). Compositions of the antibodies described herein may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed an overall beneficial course of action.

It is self-evident that the antibodies are administered to the patient in therapeutically effective amount which is the amount of the subject compound or combination that will elicit the biological or medical response of a tissue, system, animal or human that is being sought by the researcher, veterinarian, medical doctor or other clinician.

The term "in combination with" refers to the "co-administration" or "co-administering" of the anti-HER3 antibody which is administered additionally to the anti-HER2 antibody, (or anti-HER1 antibody, respectively). The "co-administration" means that the first antibody is administered additionally to the second antibody either simultaneously or sequentially. The coadministration can be simultaneous or sequential in either order, wherein preferably there is a time period while both (or all) active agents simultaneously exert their biological activities. When both antibodies are administered simultaneously the dose is administered on the same day in one administration, e.g. during one continuous infusion. When both antibodies are administered sequentially the dose is administered either on the same day in two separate administrations, e.g. two separate continuous infusions, or one of the antibodies is administered on day 1 and the second antibody is administered on day 2 to day 7, preferably on day 2 to 4. The terms "co-administration" or "co-administering" with respect to the maintenance doses of the first antibody and the second antibody mean that the maintenance doses can be either administered simultaneously, e.g. during one continuous infusion, if the treatment cycle is appropriate for both antibodies. Or the maintenance doses are administered sequentially, either within one or several days, e.g. the maintenance dose of the first antibody is administered every 3 weeks, and the maintenance dose of the second is administered every 2 weeks. Also other treatment cycles/usually from 1 to 4 weeks, preferably from 2 to 3 weeks, may be used for both antibodies.

The amount of antibody co-administration and the timing of administration will depend on the type (species, gender, age, weight, etc.) and condition of the patient being treated and the severity of the disease or condition being treated. Usually typical dosages antibodies are used. For example, the dosages for administration of the antibodies according to the invention can be about 1 μg/kg to 50 mg/kg (e.g. 0.1-20 mg/kg) of antibody by one or more separate administrations, or by continuous infusion. A typical daily dosage might range from about 1 μg/kg to about 100 mg/kg. In a preferred aspect, the antibodies are administered every two to three weeks, at a dose ranged from about 1 mg/kg to about 15 mg/kg. A preferred dose for trastuzumab is a loading dose of 4 mg/kg administered as continuous infusion and subsequent 3-weekly infusions of 2 mg/kg to 6 mg/kg, preferably 2 mg/kg, administered as continuous infusion until disease progression is detected.

In the context of this invention, additional other cytotoxic, chemotherapeutic or anti-cancer agents, or compounds that enhance the effects of such agents may be used in combination treatment of the present invention. Such agents include, for example: alkylating agents or agents with an alkylating action, such as cyclophosphamide (CTX; e.g. Cytoxan®), chlorambucil (CHL; e.g. Leukeran®), cisplatin (CisP; e.g. Platinol®) busulfan (e.g. Myleran®), melphalan, carmustine (BCNU), streptozotocin, triethylenemelamine (TEM), mitomycin C, and the like; anti-metabolites, such as methotrexate (MTX), etoposide (VP16; e.g. Vepesid®), 6-mercaptopurine (6 MP), 6-thioguanine (6TG), cytarabine (Ara-C), 5-fluorouracil (5-FU), capecitabine (e.g. Xeloda®), dacarbazine (DTIC), and the like; antibiotics, such as actinomycin D, doxorubicin (DXR; e.g. Adriamycin®), daunorubicin (daunomycin), bleomycin, mithramycin and the like; alkaloids, such as vinca alkaloids such as vincristine (VCR), vinblastine, and the like; and other antitumor agents, such as paclitaxel (e.g. Taxol®) and paclitaxel derivatives, the cytostatic agents, glucocorticoids such as dexamethasone (DEX; e.g. Decadron®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. Ethyol®), dactinomycin, mechlorethamine (nitrogen mustard), streptozocin, cyclophosphamide, lomustine (CCNU), doxorubicin lipo (e.g. Doxil®), gemcitabine (e.g. Gemzar®), daunorubicin lipo (e.g. Daunoxome®), procarbazine, mitomycin, docetaxel (e.g. Taxotere®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil. In one embodiment the combination treatment of the present invention is used without such additional cytotoxic, chemotherapeutic or anti-cancer agents, or compounds that enhance the effects of such agents.

In the context of this invention, an anti-hormonal agent may be used in combination treatment of the present invention. As used herein, the term "anti-hormonal agent" includes natural or synthetic organic or peptidic compounds that act to regulate or inhibit hormone action on tumors. Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. Fareston®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as Zoladex® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinyl-carbonyl)-D-lysyl-L-leucyl-N6-(1-methylethyl)-L-lysyl-L-proline (e.g Antide®, Ares-Serono); the LHRH antagonist ganirelix acetate; the steroidal anti-androgens cyproterone acetate (CPA) and megestrol acetate, commercially available as Megace® (Bristol-Myers Oncology); the nonsteroidal anti-androgen flutamide (2-methyl-N-[4,20-nitro-3-(trifluoromethyl) phenylpropanamide), commercially available as Eulexin® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR (retinoic acid receptor), RXR (retinoid X receptor), TR (thyroid receptor), VDR (vitamin-D receptor), and the like. In one embodiment the combination treatment of the present invention is used without such additional anti-hormonal agent.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, additional antiproliferative agents may be used in the combination treatment of the present invention, including, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217. In one embodiment the combination treatment of the present invention is used without such additional antiproliferative agents.

In the context of this invention, an effective amount of ionizing radiation may be carried out and/or a radiopharmaceutical may be used in addition to combination treatment of the present invention. The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR kinase inhibitor according to this invention is an antibody, it is also possible to label the antibody with such radioactive isotopes. In one embodiment the combination treatment of the present invention is used without such additional ionizing radiation.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination or single therapy of the invention is enhanced when combined with radiation, optionally with additional chemotherapeutic or anticancer agents. Parameters of adjuvant radiation therapies are, for example, contained in International Patent Publication WO 99/60023.

The antibodies are administered to a patient according to known methods, by intravenous administration as a bolus or by continuous infusion over a period of time, by intramuscular, intraperitoneal, intracerobrospinal, subcutaneous, intra-articular, intrasynovial, or intrathecal routes. Intravenous or subcutaneous administration of the antibodies is preferred.

The present invention further provides an article of manufacture comprising a container, a composition within the container comprising an anti-HER3 antibody and a package insert instructing the user of the composition to administer said anti-HER3 antibody to a patient suffering from HER2 normal cancer in combination with an anti-HER2 antibody which inhibits the dimerization of HER2.

The present invention further provides an article of manufacture comprising a container, a composition within the container comprising an anti-HER3 antibody and a package insert instructing the user of the composition to administer said anti-HER3 antibody to a patient suffering from cancer in combination with an anti-HER2 antibody which inhibits the dimerization of HER2.

The present invention further provides an article of manufacture comprising a container, a composition within the container comprising an anti-HER3 antibody and a package insert instructing the user of the composition to administer said anti-HER3 antibody to a patient suffering from cancer in combination with an anti-HER1 antibody wherein both, the antibody which binds to human HER3 and the antibody which binds to human HER1, are characterized in being glycosylated with a sugar chain at Asn297 whereby the amount of fucose within said sugar chain is 65% or lower.

The term "package insert" refers to instructions customarily included in commercial packages of therapeutic products, which may include information about the indications, usage, dosage, administration, contraindications and/or warnings concerning the use of such therapeutic products.

In one embodiment, the article of manufacture containers may further include a pharmaceutically acceptable carrier. The article of manufacture may further include a sterile diluent, which is preferably stored in a separate additional container.

In the following one series of embodiments of the invention is listed:

1. An antibody which binds to human HER3 for use in the treatment of cancer in combination with an antibody which binds to human HER2 and which inhibits dimerization of HER2, wherein the cancer is a HER2-normal cancer.
2. The antibody of embodiment 1, wherein the antibody which binds to human HER3 is characterized in that the heavy chain variable domain comprises a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6 or a CDR1L region of SEQ ID NO:7.
3. The antibody of embodiment 1, wherein the antibody which binds to human HER3 is characterized in that the heavy chain variable domain VH is SEQ ID NO:8; and the light chain variable domain VL is SEQ ID NO:9, or the light chain variable domain VL is SEQ ID NO:10, or the light chain variable domain VL is SEQ ID NO:11; or a humanized version thereof
4. The antibody of embodiment 1, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6.
5. The antibody of embodiment 1, wherein the antibody which binds to human HER3 is characterized in that
   the heavy chain variable domain VH is SEQ ID NO:8; and
      the light chain variable domain VL is SEQ ID NO:9, or
      the light chain variable domain VL is SEQ ID NO:11.
6. The antibody of embodiment 1, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.
7. The antibody of embodiment 1, wherein the antibody which binds to human HER3 is characterized in that
   the heavy chain variable domain VH is SEQ ID NO:8; and
      the light chain variable domain VL is SEQ ID NO:10.

8. The antibody of any one of embodiments 1 to 7, wherein the antibody which binds to human HER3 is characterized in that is glycosylated with a sugar chain at Asn297 whereby the amount of fucose within said sugar chain is 65% or lower.
9. The antibody of any one of embodiments 1 to 8, wherein the antibody which binds to human HER2 and which inhibits dimerization of HER2 is pertuzumab.
10. The antibody of any one of embodiments 1 to 9, wherein the cancer is characterized by a HER3 expression.
11. The antibody of any one of embodiments 1 to 10, wherein the cancer is breast cancer, ovarian cancer, gastric cancer, prostate cancer, pancreatic cancer or cancer of the head or neck breast cancer.

In the following another series of embodiments of the invention is listed:

1. Use of an antibody which binds to human HER3 for the manufacture of a medicament for the treatment of cancer in combination with an antibody which binds to human HER2 and which inhibits dimerization of HER2, wherein the cancer is a HER2-normal cancer.
2. The use of embodiment 1, wherein the antibody which binds to human HER3 is characterized in that the heavy chain variable domain comprises a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6 or a CDR1L region of SEQ ID NO:7.
3. The use of embodiment 1, wherein the antibody which binds to human HER3 is characterized in that
   the heavy chain variable domain VH is SEQ ID NO:8; and
      the light chain variable domain VL is SEQ ID NO:9, or
      the light chain variable domain VL is SEQ ID NO:10, or
      the light chain variable domain VL is SEQ ID NO:11; or
      a humanized version thereof.
4. The use of embodiment 1, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6.
5. The use of embodiment 1, wherein the antibody which binds to human HER3 is characterized in that
   the heavy chain variable domain VH is SEQ ID NO:8; and
      the light chain variable domain VL is SEQ ID NO:9, or
      the light chain variable domain VL is SEQ ID NO:11.
6. The use of embodiment 1, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.
7. The use of embodiment 1, wherein the antibody which binds to human HER3 is characterized in that
   the heavy chain variable domain VH is SEQ ID NO:8; and
      the light chain variable domain VL is SEQ ID NO:10.
8. The use of any one of embodiments 1 to 7, wherein the antibody which binds to human HER3 is characterized in that is glycosylated with a sugar chain at Asn297 whereby the amount of fucose within said sugar chain is 65% or lower.
9. The use of any one of embodiments 1 to 8, wherein the antibody which binds to human HER2 and which inhibits dimerization of HER2 is pertuzumab.
10. The use of any one of embodiments 1 to 9, wherein the cancer is characterized by a HER3 expression.
11. The use of any one of embodiments 1 to 10, wherein the cancer is breast cancer, ovarian cancer, gastric cancer, prostate cancer, pancreatic cancer or cancer of the head or neck breast cancer.

In the following another series of embodiments of the invention is listed:

1. A method of treating a patient suffering from a HER2-normal cancer wherein the method comprises the co-administration of an antibody which binds to human HER3 in combination with an antibody which binds to human HER2 and which inhibits dimerization of HER2.
2. The method of embodiment 1, wherein the antibody which binds to human HER3 is characterized in that the heavy chain variable domain comprises a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6 or a CDR1L region of SEQ ID NO:7.
3. The method of embodiment 1, wherein the antibody which binds to human HER3 is characterized in that
   the heavy chain variable domain VH is SEQ ID NO:8; and
      the light chain variable domain VL is SEQ ID NO:9, or
      the light chain variable domain VL is SEQ ID NO:10, or
      the light chain variable domain VL is SEQ ID NO:11; or
      a humanized version thereof
4. The method of embodiment 1, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:6.
5. The method of embodiment 1, wherein the antibody which binds to human HER3 is characterized in that
   the heavy chain variable domain VH is SEQ ID NO:8; and
      the light chain variable domain VL is SEQ ID NO:9, or
      the light chain variable domain VL is SEQ ID NO:11.
6. The method of embodiment 1, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.
7. The method of embodiment 1, wherein the antibody which binds to human HER3 is characterized in that
   the heavy chain variable domain VH is SEQ ID NO:8; and
      the light chain variable domain VL is SEQ ID NO:10.
8. The method of any one of embodiments 1 to 7, wherein the antibody which binds to human HER3 is characterized in that is glycosylated with a sugar chain at Asn297 whereby the amount of fucose within said sugar chain is 65% or lower.
9. The method of any one of embodiments 1 to 8, wherein the antibody which binds to human HER2 and which inhibits dimerization of HER2 is pertuzumab.
10. The method of any one of embodiments 1 to 9, wherein the cancer is characterized by a HER3 expression.

11. The method of any one of embodiments 1 to 10, wherein the cancer is breast cancer, ovarian cancer, gastric cancer, prostate cancer, pancreatic cancer or cancer of the head or neck breast cancer.

In the following another series of embodiments of the invention is listed:

1. An antibody which binds to human HER3 for use in the treatment of cancer in combination with an antibody which binds to human HER1, wherein at least one of the antibody which binds to human HER3 and the antibody which binds to human HER1 is characterized in that the antibody is glycosylated with a sugar chain at Asn297 whereby the amount of fucose within said sugar chain is 65% or lower.
2. The antibody of embodiment 1, wherein both, the antibody which binds to human HER3 and the antibody which binds to human HER1, are characterized in being glycosylated with a sugar chain at Asn297 whereby the amount of fucose within said sugar chain is 65% or lower.
3. The antibody of any one of embodiments 1 to 2, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.
4. The antibody of any one of embodiments 1 to 2, wherein the antibody which binds to human HER3 is characterized in that
the heavy chain variable domain VH is SEQ ID NO:8; and
the light chain variable domain VL is SEQ ID NO:10.
5. The antibody of any one of embodiments 3 to 4, wherein the antibody which binds to human HER1 is characterized in that
the heavy chain variable domain VH is SEQ ID NO:20; and
the light chain variable domain VL is SEQ ID NO:21.
6. The antibody of any one of embodiments 1 to 5, wherein the cancer is characterized by a HER3 expression.
7. The antibody of embodiment 6, wherein the cancer is characterized by a HER1 expression.
8. The antibody of any one of embodiments 1 to 8, wherein the cancer is lung cancer, breast cancer, colorectal cancer, or head and neck cancer.

In the following another series of embodiments of the invention is listed:

1. Use of an antibody which binds to human HER3 for the manufacture of a medicament for the treatment of cancer in combination with an antibody which binds to human HER1, wherein at least one of the antibody which binds to human HER3 and the antibody which binds to human HER1 is characterized in that the antibody is glycosylated with a sugar chain at Asn297 whereby the amount of fucose within said sugar chain is 65% or lower.
2. The use of embodiment 1, wherein both, the antibody which binds to human HER3 and the antibody which binds to human HER1, are characterized in being glycosylated with a sugar chain at Asn297 whereby the amount of fucose within said sugar chain is 65% or lower.
3. The use of any one of embodiments 1 to 2, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.
4. The use of any one of embodiments 1 to 2, wherein the antibody which binds to human HER3 is characterized in that
the heavy chain variable domain VH is SEQ ID NO:8; and
the light chain variable domain VL is SEQ ID NO:10.
5. The use of any one of embodiments 3 to 4, wherein the antibody which binds to human HER1 is characterized in that
the heavy chain variable domain VH is SEQ ID NO:20; and
the light chain variable domain VL is SEQ ID NO:21.
6. The use of any one of embodiments 1 to 5, wherein the cancer is characterized by a HER3 expression.
7. The use of embodiment 6, wherein the cancer is characterized by a HER1 expression.
8. The use of any one of embodiments 1 to 8, wherein the cancer is lung cancer, breast cancer, colorectal cancer, or head and neck cancer.

In the following another series of embodiments of the invention is listed:

1. A method of treating a patient suffering from a cancer wherein the method comprises the co-administration an antibody which binds to human HER3 in combination with an antibody which binds to human HER1, wherein at least one of the antibody which binds to human HER3 and the antibody which binds to human HER1 is characterized in that the antibody is glycosylated with a sugar chain at Asn297 whereby the amount of fucose within said sugar chain is 65% or lower.
2. The method of embodiment 1, wherein both, the antibody which binds to human HER3 and the antibody which binds to human HER1, are characterized in being glycosylated with a sugar chain at Asn297 whereby the amount of fucose within said sugar chain is 65% or lower.
3. The method of any one of embodiments 1 to 2, wherein the antibody which binds to human HER3 is characterized in comprising as heavy chain variable domain a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.
4. The method of any one of embodiments 1 to 2, wherein the antibody which binds to human HER3 is characterized in that
the heavy chain variable domain VH is SEQ ID NO:8; and
the light chain variable domain VL is SEQ ID NO:10.
5. The method of any one of embodiments 3 to 4, wherein the antibody which binds to human HER1 is characterized in that
the heavy chain variable domain VH is SEQ ID NO:20; and
the light chain variable domain VL is SEQ ID NO:21.
6. The method of any one of embodiments 1 to 5, wherein the cancer is characterized by a HER3 expression.
7. The method of embodiment 6, wherein the cancer is characterized by a HER1 expression.
8. The method of any one of embodiments 1 to 8, wherein the cancer is lung cancer, breast cancer, colorectal cancer, or head and neck cancer.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO: 1 heavy chain CDR3H, Mab 205.10
SEQ ID NO: 2 heavy chain CDR2H, Mab 205.10
SEQ ID NO: 3 heavy chain CDR1H, Mab 205.10
SEQ ID NO: 4 light chain CDR3L, Mab 205.10

SEQ ID NO: 5 light chain CDR2L, Mab 205.10
SEQ ID NO: 6 light chain CDR1L (variant 1), Mab 205.10
SEQ ID NO: 7 light chain CDR1L (variant 2), Mab 205.10
SEQ ID NO: 8 heavy chain variable domain VH, Mab 205.10
SEQ ID NO: 9 light chain variable domain VL, Mab 205.10.1
SEQ ID NO: 10 light chain variable domain VL, Mab 205.10.2
SEQ ID NO: 11 light chain variable domain VL, Mab 205.10.3
SEQ ID NO: 12 human kappa light chain constant region
SEQ ID NO: 13 human heavy chain constant region derived from IgG1
SEQ ID NO: 14 human heavy chain constant region derived from IgG1 mutated on L234A and L235A
SEQ ID NO: 15 human heavy chain constant region derived from IgG4
SEQ ID NO: 16 human heavy chain constant region derived from IgG4 mutated on S228P
SEQ ID NO: 17 human HER3 (including signal peptide)
SEQ ID NO: 18 human HER2 (including signal peptide)
SEQ ID NO: 19 human HER1 (including signal peptide)
SEQ ID NO: 20 heavy chain variable domain VH of anti-HER1 antibody GA201
SEQ ID NO: 21 light chain variable domain VL of anti-HER1 antibody GA201

EXAMPLES

Example 1

Immunisation

NMRI mice were immunized with hHER3-ECD (inhouse) and boosted with hu-HER3-ECD. The immune response was monitored by testing serum samples against the HER1/2/3-ECD-ELISA. Spleen cells from mice with sufficient titers of anti-HER3 immunoglobulin were frozen for later immortalization by fusion with mouse myeloma cell line P3X63 Ag8.653. One fusion was done and hybridoma supernatants screened by HER1/2/-ECD-ELISA showing no cross-reactivity, but binding to HER3-ECD and anti-HER3 selective hybridomas were selected. The relevant hybridomas were cloned by single cell FACS sorting. Single cell clones from different hybridomas were cultured in vitro to produce antibody in tissue culture medium for characterization. Antibodies were selected by determining their ability to inhibit HER3 phosphorylation, AKT phosphorylation and tumor cell proliferation of MDA-MB-175 cells (see Examples below). From the obtained antibodies, one was further humanized to give the following antibodies Mab 205.10.1, Mab 205.10.2 and Mab 205.10.3 with their respective VH and VL or CDRs.

| Antibody | VH | VL |
|---|---|---|
| Mab 205.10.1 | SEQ ID NO: 8 | SEQ ID NO: 9 |
| Mab 205.10.2 | SEQ ID NO: 8 | SEQ ID NO: 10 |
| Mab 205.10.3 | SEQ ID NO: 8 | SEQ ID NO: 11 |

| Antibody | CDR3H | CDR2H | CDR1H | CDR3L | CDR2L | CDR1L |
|---|---|---|---|---|---|---|
| Mab 205.10.1 | SEQ ID NO: 1 | SEQ ID NO: 2 | SEQ ID NO: 3 | SEQ ID NO: 4 | SEQ ID NO: 5 | SEQ ID NO: 6 |
| Mab 205.10.2 | SEQ ID NO: 1 | SEQ ID NO: 2 | SEQ ID NO: 3 | SEQ ID NO: 4 | SEQ ID NO: 5 | SEQ ID NO: 7 |
| Mab 205.10.3 | SEQ ID NO: 1 | SEQ ID NO: 2 | SEQ ID NO: 3 | SEQ ID NO: 4 | SEQ ID NO: 5 | SEQ ID NO: 6 |

In one embodiment such antibodies were prepared using constant regions of human origin e.g. SEQ ID NO:12-13.

Example 2

Binding Assays a) Antigene Specific ELISA for Binding to Human HER3ECD

Soluble human HER3 extracellular domain fused to Streptavidin Binding Protein (SBP) was captured on a sreptavidine plate. To define optimal binding of the antibody to SPB-CDCP1, 384-well polystyrene plates (NUNC, streptavidin-coated) delivered by MicroCoat, Bernried, Germany (ID-No. 1734776-001) have been coated with pure and stepwise diluted HEK293 supernatant (in BSA/IMDM buffer: 100 mg/ml BSA Fraction V, Roche 10735078001, dissolved in Iscove's Modified Dulbeccos Medium). Using mouse a calibration curve of chimeric 205 antibodies the optimal dilution factor of the HEK293 supernatant in relation to the streptavidin binding capazity of the microtiter plate was identified. For the standard coating, SBP-HER3 containing HEK293 supernatant was diluted (between 1:15 and 1:40) and incubated overnight at 2-80 C (25 μl per well). Intensive washing of the microtiter plate is necessary to remove remaining unbound SBP-HER3.

Antibodies according to the invention antibody were tested either undiluted or using a 12-step-dilution. 12.5 μl per well of each sample was incubated for 90 min at room temperature. After intensive washing using PBS-T (0.1% Tween 20 in PBS) 25 μl goat anti-human IgG antibodies coupled with HRP (Jackson ImmunoResearch, Code No: 109-036-098, dilution 1:10000) for human antibodies were added and incubated for 1 hour. After intensive washing the binding of the antibodies was detected with ABTS tablets (Roche Diagnostics GmbH, Cat. No.: 1112422). Absorbance at 405 nm/492 nm was measured using a standard photometer.

The table shows the relative binding ratios of the different antibodies.

| antibody | hu_HER3-ECD-ELISA c(μg/ml) | IgG-ELISA c(μg/ml) | activity (ratio binding to hu_HER3-ECD/IgG) |
|---|---|---|---|
| Mab 205.10.1 | 583.,1 | 785.,0 | 0.74 |
| Mab 205.10.2 | 396.,4 | 508.,0 | 0.,78 |
| Mab 205.10.3 | 505.4 | 608.4 | 0.83 | b) Characterization of the Binding of Anti-HER3 Antibodies to a Extracellular-Domain-(ECD) Fragment of Human HER3 by Biacore Analyses:

For affinity measurements, 30 μg/ml of anti Fcγ antibodies (from goat, Jackson Immuno Research) were coupled to the surface of a CM-5 sensor chip by standard amine-coupling and blocking chemistry on a SPR instrument (Biacore T100). After conjugation, anti-HER3 antibodies were injected at 25° C. at a flow rate of 5 μL/min, followed by a dilution series (0 nM to 1000 nM) of human HER3 ECD at 30 μL/min. As running buffer for the binding experiment PBS/0.1% BSA was used. The chip was then regenerated with a 60 s pulse of 10 mM glycine-HCl, pH 2.0 solution.

Calculation of thermodynamic parameters ($K_D$, binding constant to HER3) were calculated using a Langmuir 1:1 binding model.

| Antibody | Binding Affinity KD [M] |
|---|---|
| Mab 205.10.1 | $2.0 \times 10^{-9}$ |
| Mab 205.10.2 | $1.1 \times 10^{-9}$ |
| Mab 205.10.3 | $2.0 \times 10^{-9}$ |

In a competitive binding assay (Biacore) Mab205.10.1, Mab205.10.2, and Mab205.10.3 all showed binding to the same epitope. The anti-HER3-antibodies U1-7, U-53 and U1-59 described in WO 2007/077028 and Ab#6 described in WO 2008/100624 were investigated in such assay and revealed to bind to different epitopes than antibodies Mab205.10.1. Mab205.10.2, and Mab205.10.3.

Example 3 a) Inhibition of HER3 Phosphorylation in MCF7, FaDu and Mel-Juso Cells

Assays were performed in MCF7 and FaDu cells according to the following protocol: Seed cells with 500,000 cells/well into Poly-D-Lysine coated 6-well plate in RPMI1640 medium with 10% FCS. Incubate for 24 h. Remove medium by aspirating, incubate overnight with 500 µl/well RPMI 1640 with 0.5% FCS. Add antibodies in 500 µl RPMI 1640 with 0.5% FCS. Incubate for 1 h. Add HRG-1b (final concentration 500 ng/ml) for 10 min. To lyse the cells remove medium and add 80 µl ice cold Triton-X-100 cell lysis buffer and incubate for 5 minutes on ice. After transferring the lysate into 1.5 ml reaction tube and centrifugation at 14000 rpm for 15 min at 4° C., transfer supernatant into fresh reaction tubes. Samepes containing equal amounts of protein in SDS loading buffer were separated on SDS PAGE and blotted by using a semi-dry Western Blot to nitrocellulose membranes. Membranes were blocked by 1×NET-buffer+0.25% gelatine for 1 h hour and pHER3 is detected by the antibody αPhospho-HER3/ErbB3 (Tyr1289)(21D3), Cell Signaling, #4791 and HER3 by the antibody αErbB3 (C-17), Santa Cruz, #sc-285 respectively. After washing and detection of the signals by an POD coupled secondary antibody, bands were densometricaly scanned. The anti-HER3 antibodies Mab205.10.1, Mab205.10.2, and Mab205.10.3 and also anti-HER3 antibodies U1-7, U-53 and U1-59 described in WO 2007/077028 and Ab#6 described in WO 2008/100624 were investigated. Percent (%) inhibition of anti-HER3 antibodies on receptor phosphorylation in MCF7 cells is shown below and in FIG. 1A.

| % Inhibition of HER3 phosphorylation in MCF7 cells | | |
|---|---|---|
| Antibody | pHER3 % inhibition [0.1 µg/ml] | pHER3 % inhibition [1.0 µg/ml] |
| control | 0 | 0 |
| Mab205.10.2 | 62 | 96 |
| U1-7 | 36 | 44 |
| U1-53 | 54 | 51 |
| U1-59 | 15 | 70 |
| Ab#6 | 13 | 64 |

In a further experiment the anti-HER3 antibody Mab205.10.2, and also the anti-HER3-antibodies 8B8.2D9 described in WO 97/35885, and 1B4C3 and 2D1D12 described in WO 2003/013602 were investigated. Percent (%) inhibition of anti-HER3 antibodies on receptor phosphorylation in MCF7 cells is shown below and in FIG. 1B.

| % Inhibition of HER3 phosphorylation in MCF7 cells | | |
|---|---|---|
| Antibody | pHER3 % inhibition [0.1 µg/ml] | pHER3 % inhibition [1.0 µg/ml] |
| control | 0 | 0 |
| Mab205.10.2 | 68 | 91 |
| 8B8.2D9 | 13 | 28 |
| 1B4C3 | 49 | 46 |
| 2D1D12 | 34 | 34 |

Percent (%) inhibition of anti-HER3 antibodies on receptor phosphorylation in FaDu cells is shown below.

| % Inhibition of HER3 phosphorylation in FaDu cells | | | |
|---|---|---|---|
| Antibody | pHER3 % Inhibition [0.03 µg/ml] | pHER3 % Inhibition [0.10 µg/ml] | pHER3 % Inhibition [0.30 µg/ml] |
| Control | 0 | 0 | 0 |
| Mab205.10.2 | 88 | 93 | 97 |
| U1-59 | 31 | 25 | 90 |

Figure 1C:
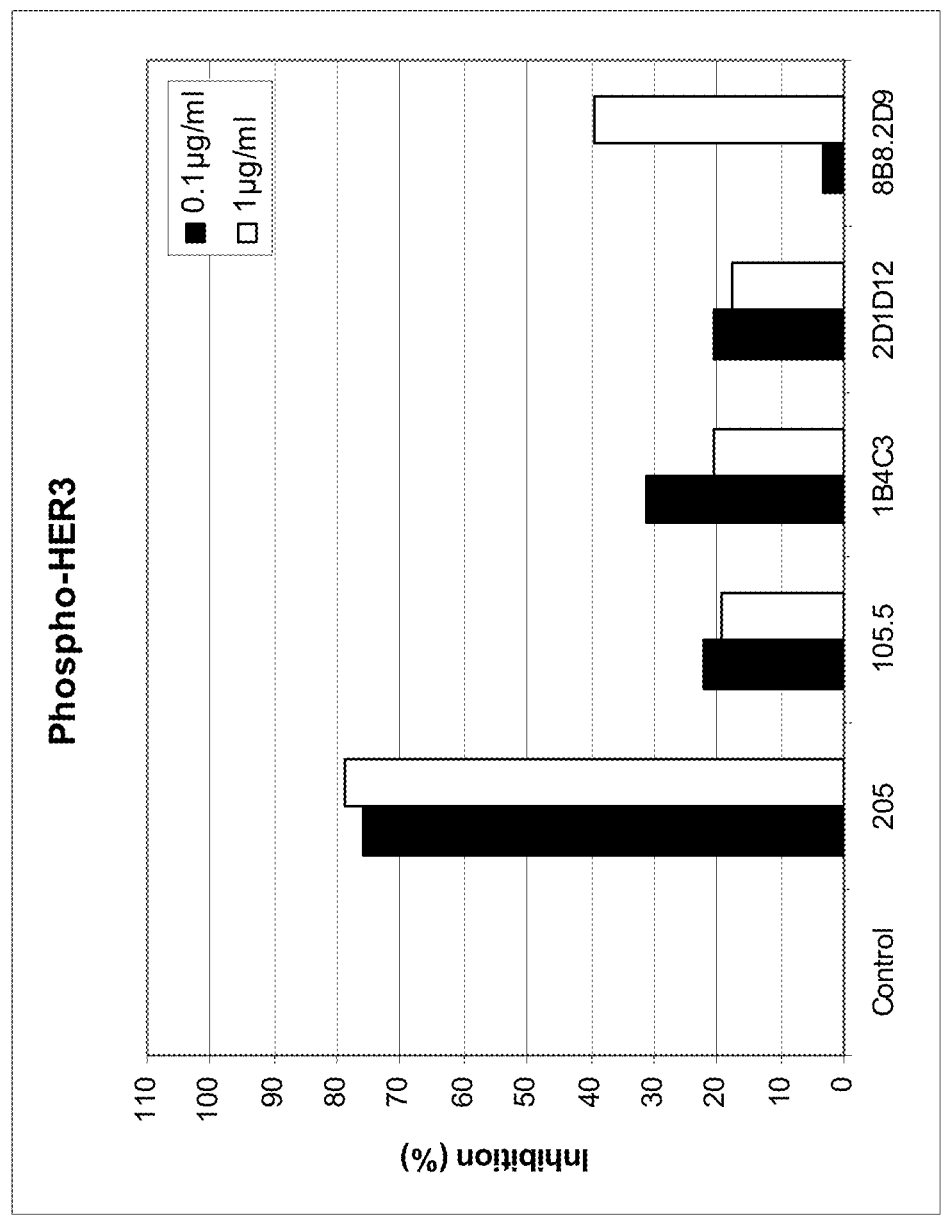

In a further experiment, the anti-HER3 antibody Mab205.10.2, and also the anti-HER3-antibodies 8B8.2D9 described in WO 97/35885, and 1B4C3 and 2D1D12 described in WO 2003/013602, and 105.5 from (Millipore, Cat. no. 05-47, named α-HER$^{ECD}$ in WO 2003/013602) were investigated in Mel-Juso cells. Assays in Mel-Juso cells were performed according to the aforementioned protocol for MCF7 and FaDu cells. Cell numbers and media volumes were adapted to 12-well plates Percent (%) inhibition of anti-HER3 antibodies on receptor phosphorylation in Mel-Juso cells is shown below and in FIG. 1C.

| % Inhibition of HER3 phosphorylation in Mel-Juso cells | | |
|---|---|---|
| Antibody | pHER3 % inhibition [0.1 µg/ml] | pHER3 % inhibition [1.0 µg/ml] |
| control | 0 | 0 |
| Mab205.10.2 | 75.9 | 78.8 |
| 105.5 (α-HER$^{ECD}$) | 22.2 | 19.5 |
| 8B8.2D9 | 31.3 | 20.3 |
| 1B4C3 | 20.7 | 17.5 |
| 2D1D12 | 3.4 | 39.3 | b) AKT Phosphorylation (ELISA)

Assays were performed in MCF7 cells according to the following protocol: Seed MCF7 cells with 30000 cells/well into Poly-D-Lysine coated 96-well plate in RPMI1640 medium with 10% FCS and incubate for 24 h. Remove medium by tapping on a clean paper towel, wash carefully with 200 µl serum-free medium, incubate overnight with 100 µl/well RPMI 1640 with 0.5% FCS. Remove medium as above; add antibodies in 100 µl RPMI 1640 with 0.5% FCS and incubate 1.5 h. Add HRG-1b (final concentration 5 ng/ml) for 10 min. Remove medium as above. To lyse the cells add 100 µl ice cold cell lysis buffer on ice and resuspend by pipetting ca.5×. Centrifuge plate at 3000 rpm for 10 min at 4°

C. and transfer 80 μl supernatant (or aliquots) into fresh polypropylene plate and shock-freeze in LN2. Store at −80° C. until assay.

AKT1,2(phospho-Ser473) EIA Kit Assay Designs #900-162:Samples (1:10 diluted) are added to the plate coated with a mouse MAB specific for the N-terminus of AKT. Incubation 1 h at RT with shaking. Wash 5×, incubation with biotinylated anti-phospho-AKT (Ser473) 1 h at RT with shaking. Wash 5×, incubation with streptavidin-HRP conjugate 30 min at RT with shaking. Wash 5×, incubate with TMB substrate 30 min at RT with shaking. Stop and read at 450 nm.

Mab 205.10.2 showed an IC50 of the AKT phosphorylation inhibition of 0.06 μg/ml.

In an pAKT ELISA in Mel-Juso cell performed as described for MCF7 cells Mab 205.10.2 showed an IC50 of AKT phosphorylation inhibition of 0.28 μg/ml all the other analyses antibodies show an IC50 above (>) 50.

| % AKT phosporylation inhibition in Mel-Juso cells | |
| --- | --- |
| Antibody | IC50 [μg/ml] |
| Mab 205.10.2 | 0.28 |
| 105.5 (α-HER$^{ECD}$) | 0.81 |
| 1B4C3 | >50 |
| 2D1D12 | >50 |
| 8B8D9 | >50 | c) Inhibition of Tumor Cell Proliferation

The anti-tumor efficacy of HER3 antibodies Mab205.10.1, Mab205.10.2, and Mab205.10.3 in a cell proliferation assay, using MDA-MB-175 cells (VII Human Breast Carcinoma Cells, ATCC catalog no. HTB-25), was assessed. 20,000 cells per well were seeded into sterile 96 well tissue culture plates with DMEM/F12 cell culture medium, containing 10% FCS and incubated at 37° C.±1° C. with 5%±1% $CO_2$ for one day. The cells are slow growing cells with a doubling time of ca. 1.5 days. Anti-HER3 antibodies were added in dilution series and further incubated for 6 days. Cell viability was then assessed using the AlamarBlue® readout. If the cell viability was reduced to more than 50% of control, IC50 values were calculated using means of triplicates for each antibody concentration; otherwise, if the % inhibition of cell viability at the highest concentration was below 50%, no IC50 could be calculated and it is indicated that $IC_{50}$ [μg/ml] is above (>) the highest concentration. Also the anti-HER3-antibodies U1-59 described in WO 2007/077028 and Ab#6 described in WO 2008/100624 were investigated.

| antibody | $IC_{50}$ [μg/ml] |
| --- | --- |
| Mab205.10.1 | 8.0 |
| Mab205.10.2 | 3.8 |
| Mab205.10.3 | 6.8 |
| U1-59 | 12.4 |
| Ab#6 | >60 μg/ml |

In a further experiment the anti-HER3 antibodies 8B8.2D9 described in WO 97/35885, and 1B4C3 described in WO 2003/013602 were investigated.

| antibody | $IC_{50}$ [μg/ml] |
| --- | --- |
| 8B8.2D9 | >100 μg/ml (29% inhibition at 100 μg/ml) |
| 1B4C3 | >100 μg/ml (26% inhibition at 100 μg/ml) |

Example 5

In Vitro ADCC in KPL-4 Tumor Cells by 1 μg/ml specLysis %

The target cells KPL4 (ADCC), breast carcinoma, cultivation in RPMI1640+2 mM L-alanyl-L-Glutamine+10% FCS) were collected with trypsin/EDTA (Gibco #25300-054) in exponential growth phase. After a washing step and checking cell number and viability, the aliquot needed was labeled for 30 min at 37° C. in the cell incubator with calcein (Invitrogen #C3100MP; 1 vial was resuspended in 50 μl DMSO for 5 Mio cells in 5 ml medium). Afterwards, the cells were washed three times with AIM-V medium, the cell number and viability was checked and the cell number adjusted to 0.3 Mio/ml.

Meanwhile, PBMC (Peripheral Blood Mononuclear Cells) as effector cells were prepared by density gradient centrifugation (Histopaque-1077, Sigma #H8889) according to the manufacturer's protocol (washing steps 1× at 400 g and 2× at 350 g 10 min each). The cell number and viability was checked and the cell number adjusted to 15 Mio/ml.

100 μl calcein-stained target cells were plated in round-bottom 96-well plates, 50 μl diluted, afucosylated antibody (Mab205.10.1, Mab205.10.2, Mab205.10.3, preparation see below) which was added and 50 μl effector cells. In some experiments the target cells were mixed with Redimune® NF Liquid (ZLB Behring) at a concentration of 10 mg/ml Redimune.

As controls served the spontaneous lysis, determined by co-culturing target and effector cells without antibody and the maximal lysis, determined by 1% Triton X-100 lysis of target cells only. The plate was incubated for 4 hours at 37° C. in a humidified cell incubator.

The killing of target cells was assessed by measuring LDH (Lactate Dehydrogenase) release from damaged cells using the Cytotoxicity Detection kit (LDH Detection Kit, Roche #1 644 793) according to the manufacturer's instruction. Briefly, 100 μl supernatant from each well was mixed with 100 μl substrate from the kit in a transparent flat bottom 96 well plate. The Vmax values of the substrate's colour reaction was determined in an ELISA reader at 490 nm for at least 10 min. Percentage of specific antibody-mediated killing was calculated as follows: ((A−SR)/(MR−SR)×100, where A is the mean of Vmax at a specific antibody concentration, SR is the mean of Vmax of the spontaneous release and MR is the mean of Vmax of the maximal release.

As additional readout the calcein retention of intact target cells was assessed by lysing the remaining target cells in borate buffer (5 mM sodium borate+0.1% Triton) and measuring the calcein fluorescence in a fluorescence plate reader. Mab205.10.1, Mab205.10.2, Mab205.10.3 showed and ADCC [KPL-4] by 1 μg/ml of specific Lysis of about 40-60%.

The afucosylated antibody (Mab205.10.1, Mab205.10.2, Mab205.10.3) were prepared by co-transfection with four plasmids, two for antibody expression, one for a fusion GnTIII polypeptide expression (a GnT-III expression vector), and one for mannosidase II expression (a Golgi mannosidase II expression vector) at a ratio of 4:4:1:1, respectively in HEK293 or CHO cells.

The full antibody heavy and light chain DNA sequences were subcloned into mammalian expression vectors (one for the light chain and one for the heavy chain) under the control of the MPSV promoter and upstream of a synthetic polyA site, each vector carrying an EBV OriP sequence. Antibodies were produced by co-transfecting HEK293-EBNA cells or CHO cells with the antibody heavy and light chain expression vectors using a calcium phosphate-transfection approach. Exponentially growing HEK293-EBNA cells were transfected by the calcium phosphate method. For the production of the glycoengineered antibody, the cells were co-transfected with four plasmids, two for antibody expression, one for a fusion GnTIII polypeptide expression (a GnT-III expression vector), and one for mannosidase II expression (a Golgi mannosidase II expression vector) at a ratio of 4:4:1:1, respectively. Cells were grown as adherent monolayer cultures in T flasks using DMEM culture medium supplemented with 10% FCS, and were transfected when they were between 50 and 80% confluent. For the transfection of a T150 flask, 15 million cells were seeded 24 hours before transfection in 25 ml DMEM culture medium supplemented with FCS (at 10% V/V final), and cells were placed at 37° C. in an incubator with a 5% CO2 atmosphere overnight. For every antibody to be produced, a solution of DNA, CaCl2 and water was prepared by mixing 188 mg total plasmid vector DNA (four plasmids, two for antibody expression (one light chain and one heavy chain), one for a fusion GnTIII polypeptide expression (a GnT-III expression vector), and one for mannosidase II expression (a Golgi mannosidase II expression vector) at a ratio of 4:4:1:1, respectively), water to a final volume of 938 µl and 938 µl of a 1M CaCl2 solution. To this solution, 1876 µl of a 50 mM HEPES, 280 mM NaCl, 1.5 mM Na2HPO4 solution at pH 7.05 were added, mixed immediately for 10 sec and left to stand at room temperature for 20 sec. The suspension was diluted with 46 ml of DMEM supplemented with 2% FCS, and divided into two T150 flasks in place of the existing medium.

The cells were incubated at 37° C., 5% CO2 for about 17 to 20 hours, then medium was replaced with 25 ml DMEM, 10% FCS. The conditioned culture medium was harvested 7 days post-transfection by centrifugation for 15 min at 210×g, the solution was sterile filtered (0.22 µm filter) and sodium azide in a final concentration of 0.01% w/v was added, and kept at 4° C.

The secreted afucosylated antibodies were purified and the oligosaccharides attached to the Fc region of the antibodies were analysed e.g. by MALDI/TOF-MS (as described in e.g. WO 2008/077546). For this analysis oligosaccharides were enzymatically released from the antibodies by PNGaseF digestion, with the antibodies being either immobilized on a PVDF membrane or in solution. The resulting digest solution containing the released oligosaccharides either prepared directly for MALDI/TOF-MS analysis or was further digested with EndoH glycosidase prior to sample preparation for MALDI/TOF-MS analysis. The analyzed amount of fucose within the sugar chain at Asn297 was between 50-20%.

Example 6

In Vivo Antitumor Efficacy of Anti-HER3 Monotherapy

The in vivo antitumor efficacy of the antibodies Mab205.10.1, Mab205.10.2, Mab205.10.3 could be detected in cell and fragment based models of various tumor origin (e.g. lung cancer, SCCHN, breast- and pancreatic cancer) transplanted on SCID beige or nude mice. As examples data are shown for the SCCHN xenograft model FaDu (cell line based), breast cancer model MAXF449 (fragment-based) and NSCLC model 7177 (fragment-based).

Test Agents

Afucosylated Mab205.10.2 (designated Mab 205 in FIGS. 2, 3, 4) was provided as stock solution from Roche, Penzberg, Germany. Antibody buffer included histidine. Antibody solution was diluted appropriately in buffer from stock prior injections.

Cell Lines and Culture Conditions

FaDu human HNSCC cells were originally obtained from ATCC. The tumor cell line was routinely cultured in MEM Eagle medium supplemented with 10% fetal bovine serum, 2 mM L-glutamine, 1 mM sodium pyruvate and 0.1 mM NEAA at 37° C. in a water-saturated atmosphere at 5% $CO_2$. Culture passage was performed with trypsin/EDTA 1× splitting every third day.

Tumor Fragments

Tumor fragments were originally taken from patients and transplanted s.c. to nude donor mice. Subsequently tumor fragments are serial passaged in vivo. For a preclinical study small tumor fragments were generated from donor mice and placed s.c. on further nude mice (MAXF449, 7177).

Animals

Female SCID beige or nude mice were purchased from breeder (e.g. Charles River, Sulzfeld, Germany) and maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum.

Monitoring

Animals were controlled daily for clinical symptoms and detection of adverse effects. For monitoring throughout the experiment body weight of animals was documented.

Treatment of Animals

Animal treatment started after animal randomisation after cell or fragment transplantation when median tumor size was about 100-150 mm³. Antibody was administered as single agent at 10 or 25 mg/kg i.p. q7d once weekly for 3-6 weeks depending of the model. The corresponding vehicle was administered on the same days.

Antibody Efficacy

A) FaDu HNSCC Xenograft

FaDu HNSCC (head and neck squamous cell cancer) xenograft bearing mice were treated with antibody Mab205.10.2 from study day 14 to 35. As a result, treatment with the Mab205.10.2 antibody showed significant anti-tumor efficacy with tumors stasis of s.c. FaDu xenografts. The Tumor Growth Inhibition (TGI) was calculated at 98%.

Figure 2:
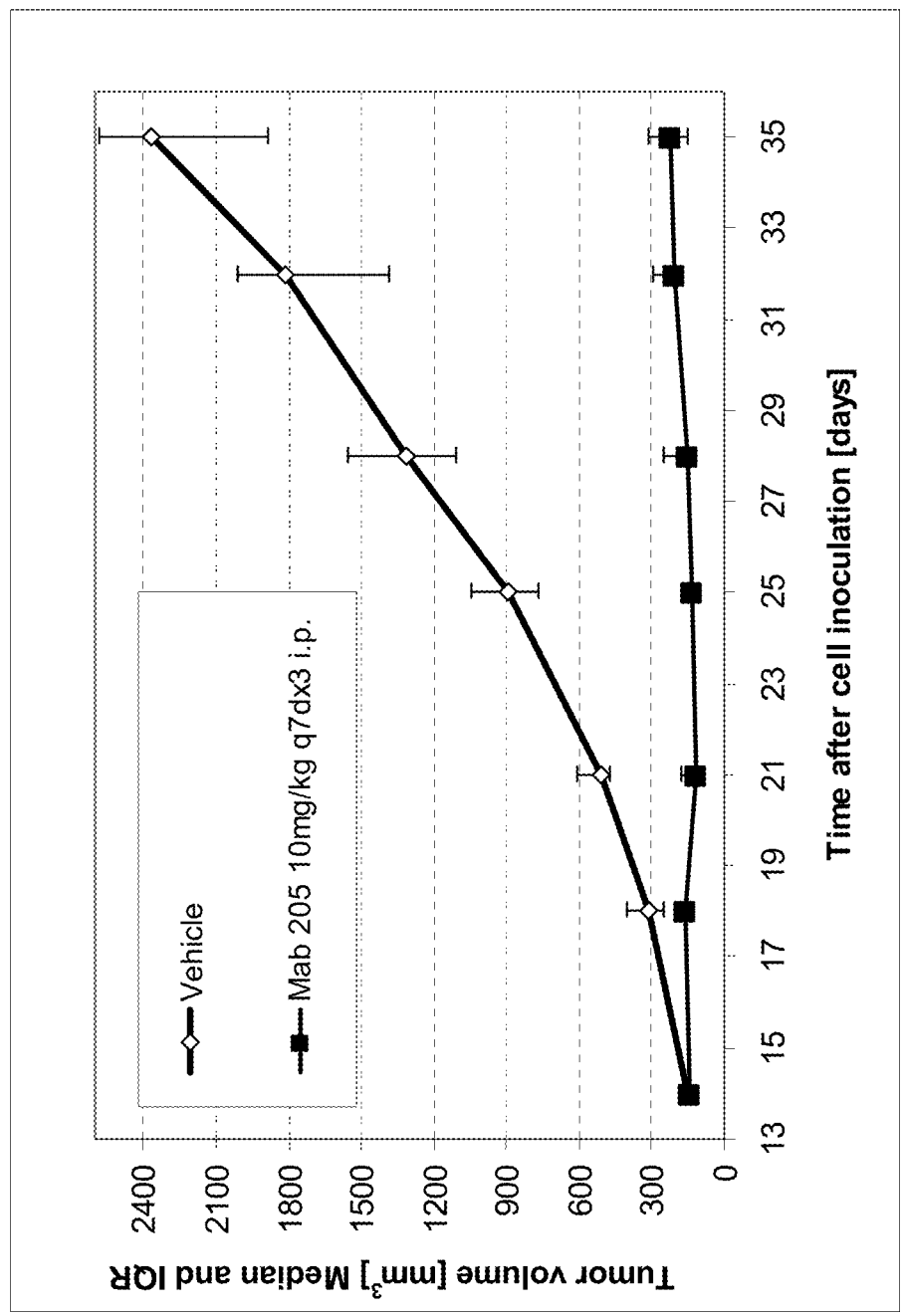
FIG. 2 Treatment with Mab 205 (10 mg/kg q7dx3, i.p.) resulted in tumor stasis of head and neck cancer FaDu SCCHN transplanted xenografts.

Treatment with Mab 205 (10 mg/kg q7dx3, i.p.) resulted in tumor stasis of FaDu HNSCCHN transplanted xenografts (see FIG. 2).

B) MAXF449 Breast Cancer Xenograft

MAXF449 breast cancer xenograft bearing mice were treated with antibody Mab205.10.2 from study day 64 to 91. As a result, treatment with the Mab205.10.2 antibody showed significant anti-tumor efficacy with tumors stasis of MAXF449 xenografts. The Tumor Growth Inhibition (TGI) was over 100%.

Figure 3:
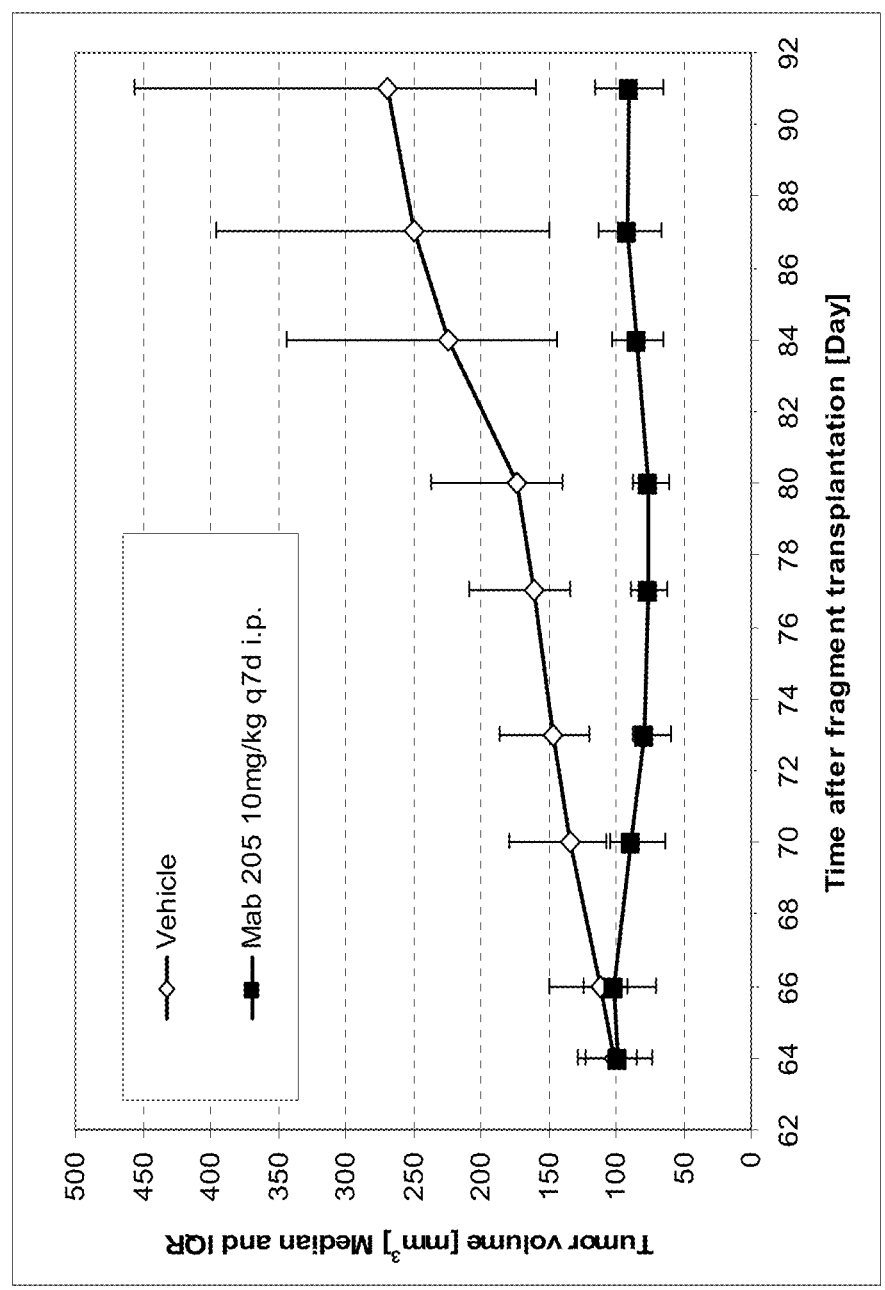
FIG. 3 Treatment with Mab 205 (10 mg/kg q7d, i.p.) resulted in tumor stasis of HER2-normal MAXF449 breast cancer transplanted xenografts.

Treatment with Mab 205 (10 mg/kg q7d, i.p.) resulted in tumor stasis of MAXF449 breast cancer transplanted xenografts (see FIG. 3).

C) 7177 NSCLC Xenograft

7177 NSCLC xenograft bearing mice were treated with antibody Mab205.10.2 from study day 28 to 56. As a result, treatment with the Mab205.10.2 antibody showed significant anti-tumor efficacy with tumors stasis of 7177 NSCLC xenografts. The Tumor Growth Inhibition (TGI) was over 100%.

Figure 4:
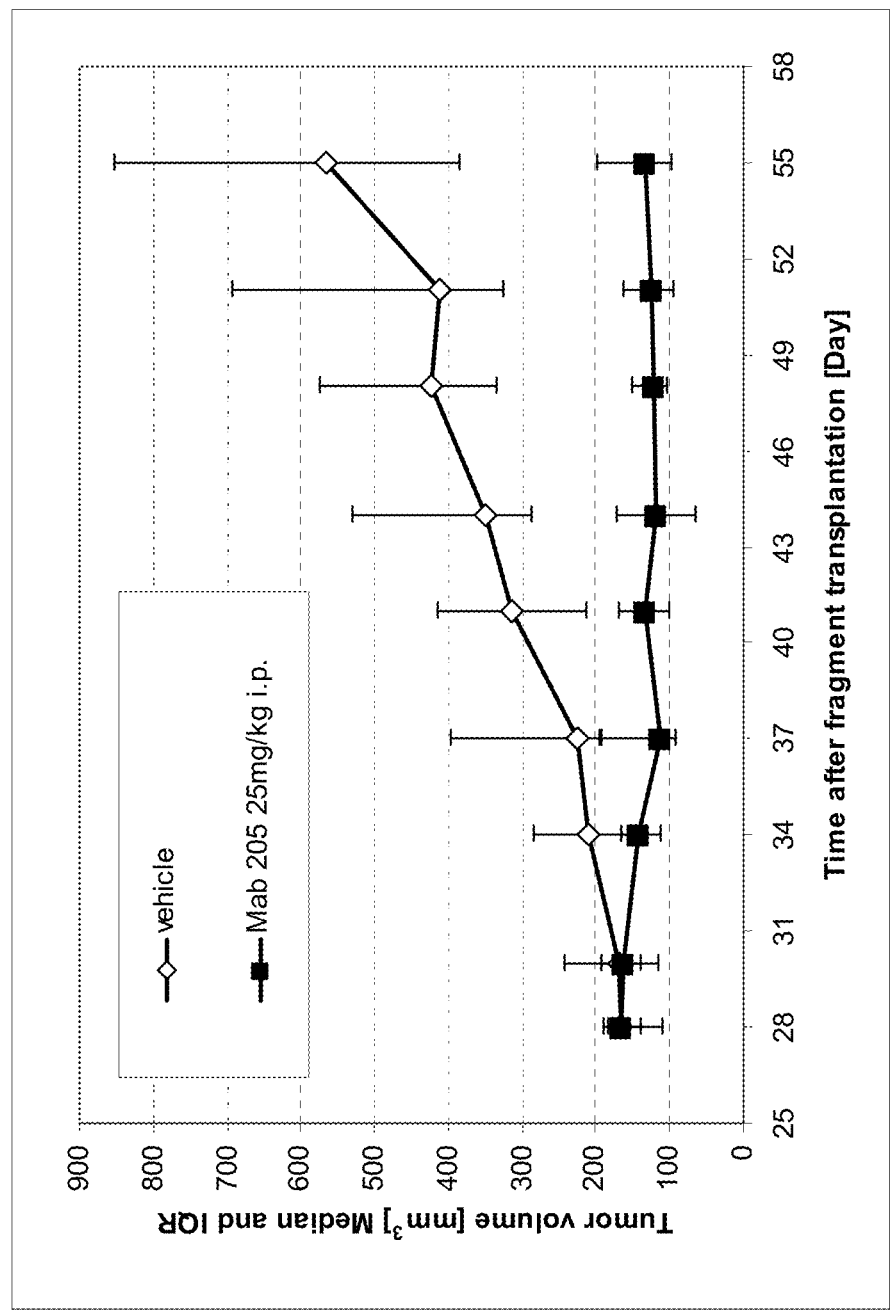
FIG. 4 Treatment with Mab 205 (25 mg/kg q7d, i.p.) resulted in tumor stasis of 7177 NSCLC transplanted xenografts.

Treatment with Mab 205 (25 mg/kg q7d, i.p.) resulted in tumor stasis of 7177 NSCLC transplanted xenografts (see FIG. 4).

Example 7

In Vivo Antitumor Efficacy of Anti-HER3 Therapy in Combination with Pertuzumab

The human breast cancer cell line ZR-75-1, which is a HER2 normal cancer cell line and expresses HER3, was subcutaneously (s.c.) inoculated into the right flank of female Balb/c nude mice ($5 \times 10^6$ cells per animal). Animals were systemically supplemented with 17β-estradiol pellets and the antibiotic cefocein (20 mg/kg) was administered s.c. in once-weekly intervals throughout the whole study period.

On day 40 after tumor cell inoculation, animals were randomized and allocated to 3 treatment groups and one vehicle group, resulting in a median tumor volume of ~100 mm$^3$ in all groups. On the day of randomization, treatment was started in once-weekly intervals by intra-peritoneal administration of Mab205.10.2 (10 mg/kg), pertuzumab (30 mg/kg loading dose followed by a 15 mg/kg maintenance dose), a combination of Mab205.10.2 plus pertuzumab. Animals were sacrificed on day 81, which was 41 days after start of treatment and 6 days after the last (6$^{th}$) medication.

Primary tumor volume (TV) was calculated according to the NCI protocol (TV=(length×width$^2$)/2), where "length" and "width" are long and short diameters of tumor mass in mm (Corbett et al., 1997). Calculation was executed from staging (day 40 after tumor inoculation) until study termination (day 81 after tumor inoculation).

For calculation of percentage tumor growth inhibition (TGI) during the treatment period, every treated group was compared with its respective vehicle control. TV$_{day\ z}$ represents the tumor volume of an individual animal at a defined study day (day z) and TV$_{day\ x}$ represents the tumor volume of an individual animal at the staging day (day x).

The following formula was applied:

$$TGI[\%] = 100 - \frac{\text{median}(TV(\text{treated})_{day\ z} - TV(\text{treated})_{day\ x}}{\text{median}(TV(\text{resp. control})_{day\ z} - TV(\text{resp. control})_{day\ x}} \times 100$$

Results/Efficacy of Treatment on Tumor Volume, Day 81

| Compound | TGI (%) |
|---|---|
| anti-HER2 Pertuzumab i.p. | 32.9 |
| anti-HER3 Mab205.10.2 i.p. | 27.6 |
| anti-HER3 Mab205.10.2 i.p. + anti-HER2 Pertuzumab i.p. | 53.2 |

Example 8

In Vivo Antitumor Efficacy of Anti-HER3 (Mab205.10.2=RG7116) Therapy in Combination with Pertuzumab Subcutaneous xenograft models were generated by using either human tumor cell lines (BxPC3, QG56, A549, NCI-H322M, NCI-H1975, HCC827, HCC827GR, NCI-H441, FaDu) or by implantation of human tumor tissue fragments. Cell lines and fragments were selected based on a high pHER3/HER3 ratio (analyzed by Western blot). All experiments were conducted according to the guidelines of the German Animal Welfare Act (Tierschutzgesetz).

For cell line-based xenograft models, cells ($5\text{-}10 \times 10^6$ cells) were injected subcutaneously (s.c.) into female SCID/beige (BxPC3, QG56, A549, NCI-H322M, NCI-H441, FaDu) or Balb/c nude mice (HCC827, HCC827GR, NCI-H1975) (both Charles River, Germany). Mice (n=10 per group) were randomized on Day 21-24 (depending on the model) stratified for primary tumor size with treatment beginning thereafter. Mab205.10.2 (abbreviated in this example as RG7116) treatments (dose 10-25 mg/kg) (n=2-5 doses) were given once weekly intraperitoneally (i.p.). Saline was used as vehicle control. Tumor volume was measured by caliper once weekly (½ (length×(width)2)) and the percentage tumor growth inhibition (TGI) compared with control animals was calculated as described in the Supplemental Material.

Subcutaneous patient-derived tumor xenografts models (PDX) were evaluated at Oncontest GmbH (Freiburg, Germany) or Experimental Pharmacology & Oncology Berlin-Buch GmbH (Berlin, Germany) by transplantation of small human tumor fragments onto NMRI nude mice. Mice were randomized (n=10 per group) and therapy performed similar to cell based models.

An orthotopic cell line-based xenograft mouse model was used to assess the contribution of ADCC. Therefore, HER3 recombinant A549-B34 transfectant cells were injected i.v. ($3 \times 10^6$ cells) into female SCID-beige mice (Taconics). Mice were randomized on Day 23 (n=15 per group) when evidence of tumor growth in the lung was confirmed in scout animals. Mice received 10-13 weekly i.p. injections of 25 mg/kg RG7116 or non-glycoengineered RG7116 or saline control. The termination criterion was sickness with locomotion impairment. Median survival was defined as the experimental day when at least 50% of animals in the group were sacrificed. Survival data were represented using Kaplan-Meier curves and differences in median survival between each treatment group were compared by means of the Pairwise Log-Rank test.

RG7116 Treatment Results in Strong TGI of Mouse Xenograft Tumors

The in vivo activity of RG7116 was investigated using subcutaneous mouse xenograft models representing different tumor entities (pancreas, TNBC, SSCHN and NSCLC). All models expressed HER3 which is significantly phosphorylated, indicating that HER3 is activated in these models;

therefore cell growth could be dependent on HER3 signaling. Since subcutaneous xenograft models lack immune effector cells at the site of the tumor, these models reflect only anti-tumor efficacy mediated via HER3 signaling inhibition; there is no contribution from ADCC.

Figure 6:
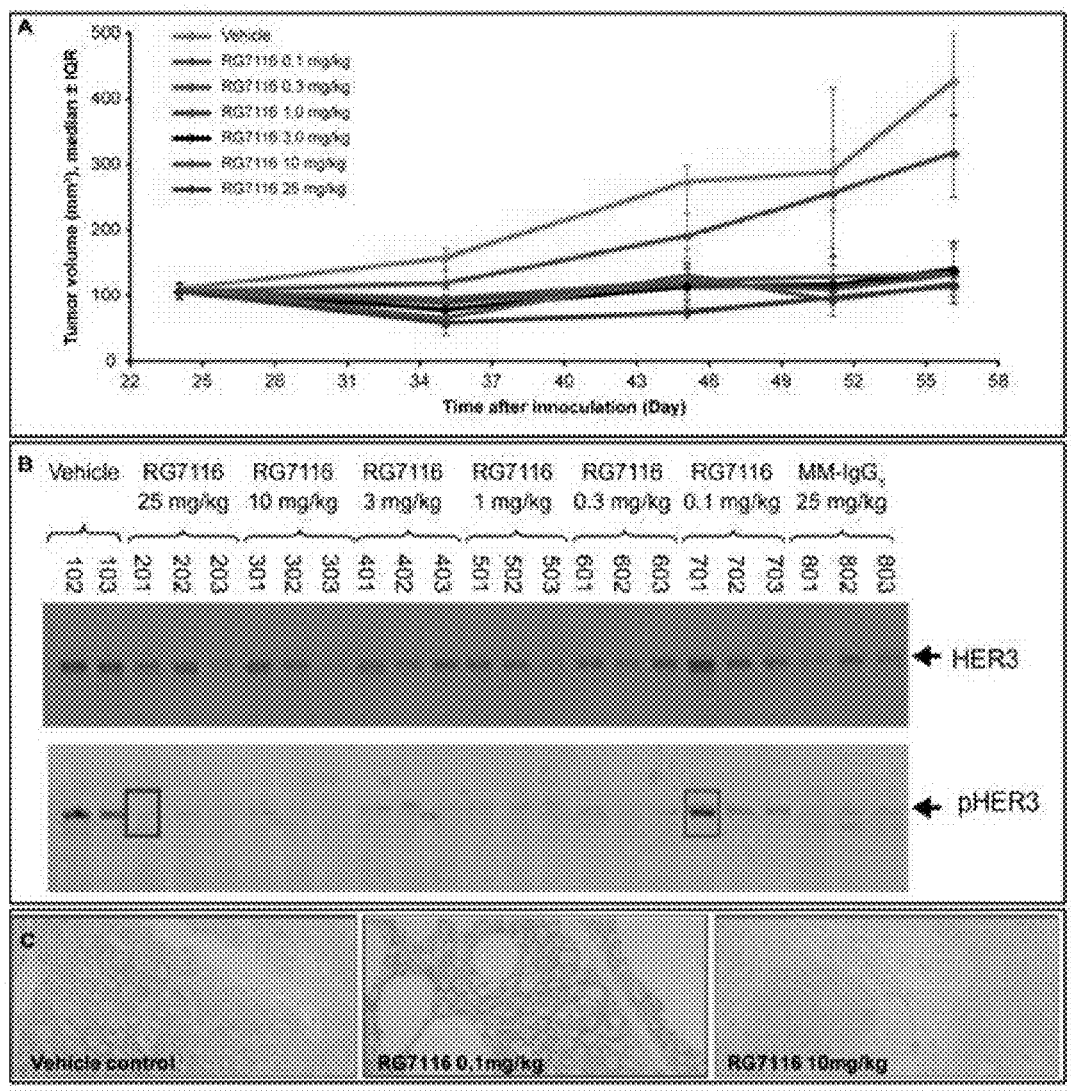
FIG. 6 In vivo efficacy of RG7116 in SCID-beige mice (n=10 per group) bearing BxPC3 human pancreatic adenocarcinoma subcutaneous xenografts. (A) Mice were treated with five weekly i.p. doses of RG7116 beginning on Day 24 and tumor size measured by caliper. RG7116 at 0.3 mg/kg and above was highly efficacious and significantly inhibited tumor growth. Mice were sacrificed on day 56 and explanted tumor tissue was examined by Western blotting for expression of HER3 and pHER (B) and for HER3 expression by immunohistochemistry (C). Efficacious doses of RG7116 inhibited HER3 phosphorylation and down-modulated membrane HER3 levels.

RG7116 demonstrated dose-dependent TGI in a BxPC3 mouse xenograft model (FIG. 6A). Intraperitoneal doses of RG7116 in the range 0.3 to 25 mg/kg were highly efficacious and resulted in TGI of >90% compared with control mice. Only at a dose of 0.1 mg/kg was partial TGI achieved. At the end of the study (Day 56) mice were sacrificed and explanted tumor tissue examined for the presence of HER3 and pHER3. Levels of pHER3 were markedly reduced in mice treated with single-agent RG7116 at doses of 0.3-25 mg/kg compared control animals (FIG. 4B). Only the non-efficacious dose (0.1 mg/kg) of RG7116 failed to inhibit HER3 phosphorylation completely. When explanted tissue was examined by immunohistochemistry, the efficacious doses of RG7116 appeared to down-modulate levels of membrane HER3 compared with tumor explants treated with vehicle control and 0.1 mg/kg RG7116 (FIG. 4C), with the same kinetics as seen with Western blotting.

Figure 5:
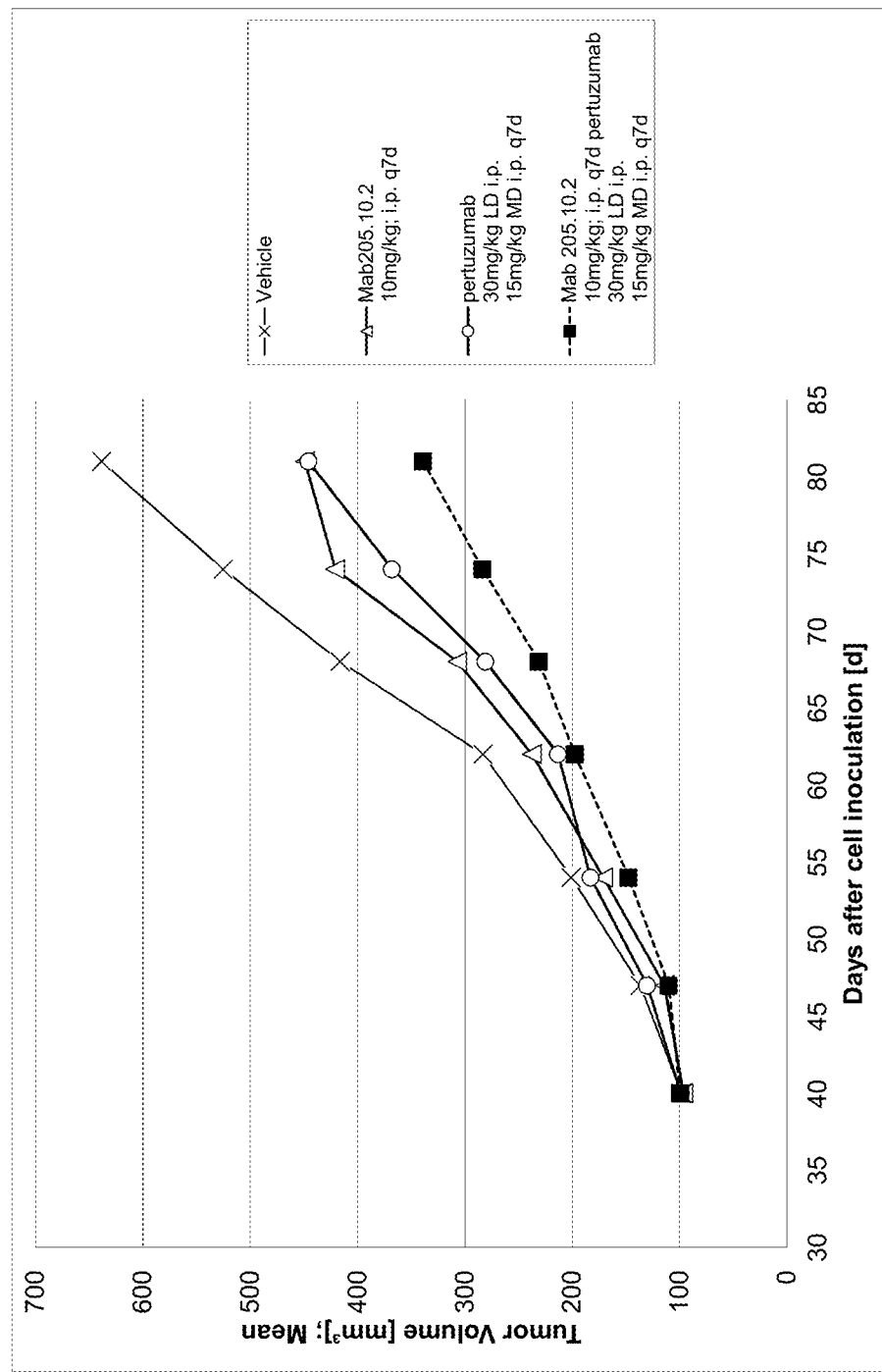
FIG. 5 Treatment of HER2-normal breast cancer cell ZR-75-1 xenografts with Mab 205.10.2 in combination with pertuzumab resulted in tumor growth inhibition.
Figure 7:
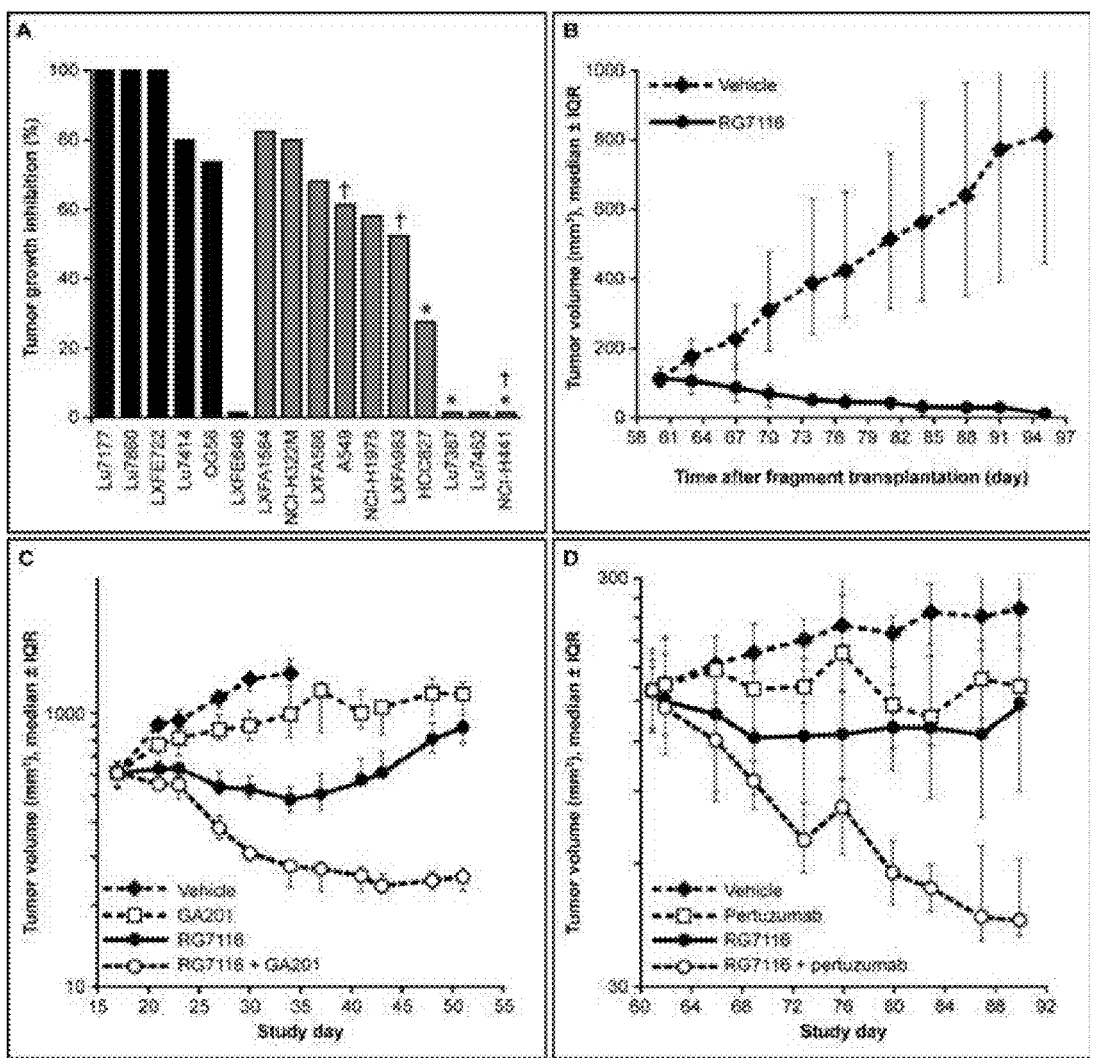
FIG. 7 Tumor growth inhibition mediated by HER3 signal inhibition. (A) NSCLC cell lines or patient-derived tumor tissue fragments established as s.c. xenografts in SCID-beige or Balb/c nude mice (n=10 per group) and treated with 4-6 weekly doses of RG7116 (10-25 mg/kg). Substantial TGI was seen in squamous lung models shown as black bars (including complete remission in half the xenograft models examined) and in adenocarcinoma models shown as grey bars (* indicates c-Met high overexpressing models, † indicates KRAS-mutant models). (B) Time course for one of the patient-derived squamous tumor xenografts (LXFE772) in which complete remission was achieved with 6 cycles of 22 mg/kg RG7116. Tumors were undetectable by Day 95. Combination of RG7116 with other anti-HER antibodies enhanced efficacy. Complete tumor regression was achieved when RG7116 was combined with GA201 (a glycoengineered anti-HER1 antibody (EGFR)) in an s.c. head and neck xenograft model (FaDu cells.

In HER3-positive human NSCLC (adenocarcinoma and squamous) models (cell line and fragment based), single-agent RG7116 induced potent TGI (FIG. 7). Treatment with 4-6 cycles of weekly RG7116 at doses of 10-25 mg/kg resulted in strong TGI in 5/6 squamous NSCLC models, including tumor stasis or complete remission in 3/6 (FIG. 7A). FIG. 5B shows an example squamous NSCLC model (LXFE722) in which complete remission was achieved. In the LXFE646 model, where single-agent RG7116 did not inhibit tumor growth, tumor stasis was achieved when RG7116 was combined with a HER1 targeted therapy (data not shown). Substantial TGI (>50%) was also observed in 5/10 adenocarcinoma NSCLC xenograft models (FIG. 7A).

c-Met expression status and KRAS mutation status were known for all of the NSCLC tumor models. The efficacy of RG7116 mediated by HER3 signal inhibition was low in the three adenocarcinoma cell lines that overexpressed c-Met (HCC827, Lu7397 and NCI-H441), whereas TGI of >50% was seen in two KRAS-mutant models (A549 and LXFA983). No TGI was seen in the third KRAS-mutant cell line (NCI-H441) which also overexpressed c-Met.

Furthermore, the efficacy of RG7116 was enhanced when combined with antibodies targeting HER1 (RG7160 [GA201]; FIG. 7C) or HER2 (pertuzumab; FIG. 7D) in models in which HER1 (FaDu cells, expresses HER1) or HER2 (MAXF449 cells, HER2-normal cancer cells) is the preferred heterodimerisation partner respectively. In both instances, combination treatment led to long lasting and complete tumor regression.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

We claim:

1. A method of treating a patient suffering from a HER2-normal cancer wherein the method comprises the co-administration of an antibody which binds to human HER3 in combination with an antibody which binds to human HER2 and which inhibits dimerization of HER2, wherein the antibody which binds to human HER3 comprises a heavy chain variable domain comprising a CDR3H region of SEQ ID NO: 1, a CDR2H region of SEQ ID NO: 2, and a CDR1H region of SEQ ID NO:3, and a light chain variable domain comprising a CDR3L region of SEQ ID NO: 4 a CDR2L region of SEQ ID NO:5, and a CDR1L region of SEQ ID NO:6 or a CDR1L region of SEQ ID NO:7.

2. The method of claim 1, wherein the antibody which binds to human HER3 is characterized in that the heavy chain variable domain comprises a CDR3H region of SEQ ID NO: 1, a CDR2H region of SEQ ID NO: 2, and a CDR1H region of SEQ ID NO:3, and the light chain variable domain comprises a CDR3L region of SEQ ID NO: 4, a CDR2L region of SEQ ID NO:5, and a CDR1L region of SEQ ID NO:7.

3. The method of claim 1, wherein the antibody which binds to human HER3 is characterized in that
the heavy chain variable domain VH is SEQ ID NO:8; and
the light chain variable domain VL is SEQ ID NO:10.

4. The method of claim 1, wherein the antibody which binds to human HER3 is characterized in that it is glycosylated with a sugar chain at Asn297 whereby the amount of fucose within said sugar chain is 65% or lower.

5. The method of claim 1, wherein the antibody which binds to human HER2 and which inhibits dimerization of HER2 is pertuzumab.

6. The method of claim 1, wherein the cancer is characterized by a HER3 expression.

7. The method of claim 1, wherein the cancer is breast cancer, ovarian cancer, gastric cancer, prostate cancer, pancreatic cancer or cancer of the head or neck breast cancer.

8. A method of treating a patient suffering from a cancer which expresses HER3 or HER1 or both HER3 and HER1 wherein the method comprises the co-administration of an antibody which binds to human HER3 in combination with an antibody which binds to human HER1, wherein at least one of the antibody which binds to human HER3 and the antibody which binds to human HER1 is characterized in that the antibody is glycosylated with a sugar chain at Asn297 whereby the amount of fucose within said sugar chain is 65% or lower, and wherein the antibody which binds to human HER3 comprises a heavy chain variable domain comprising a CDR3H region of SEQ ID NO: 1, a CDR2H region of SEQ ID NO: 2, and a CDR1H region of SEQ ID NO:3, and a light chain variable domain comprising a CDR3L region of SEQ ID NO: 4, a CDR2L region of SEQ ID NO:5, and a CDR1L region of SEQ ID NO:7.

9. The method of claim 8, wherein both the antibody which binds to human HER3 and the antibody which binds to human HER1, are characterized in being glycosylated with a sugar chain at Asn297 whereby the amount of fucose within said sugar chain is 65% or lower.

10. The method of claim 8, wherein the antibody which binds to human HER3 is characterized in that
the heavy chain variable domain VH is SEQ ID NO:8; and
the light chain variable domain VL is SEQ ID NO:10.

11. The method of claim 8, wherein the antibody which binds to human HER1 is characterized in that
the heavy chain variable domain VH is SEQ ID NO:20; and
the light chain variable domain VL is SEQ ID NO:21.

12. The method of claim 10, wherein the antibody which binds to human HER1 is characterized in that
the heavy chain variable domain VH is SEQ ID NO:20; and
the light chain variable domain VL is SEQ ID NO:21.

13. The method of claim 8, wherein the cancer is lung cancer or breast cancer, colorectal cancer, or head and neck cancer.

14. The method of claim 8, wherein the cancer expresses HER3 and HER1.

15. The method of claim 12, wherein the cancer expresses HER3 and HER1.

* * * * *